(12) United States Patent
Nimlos et al.

(10) Patent No.: US 10,364,322 B2
(45) Date of Patent: Jul. 30, 2019

(54) NAPHTHALENE-CONTAINING POLYMERS AND METHODS OF MAKING THE SAME

(71) Applicant: Alliance for Sustainable Energy, LLC, Golden, CO (US)

(72) Inventors: Mark R. Nimlos, Golden, CO (US); Andrew Nolan Wilson, Denver, CO (US); Calvin Mukarakate, Arvada, CO (US); Mariel Jene Price, Sacramento, CA (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 79 days.

(21) Appl. No.: 15/879,840

(22) Filed: Jan. 25, 2018

(65) Prior Publication Data

US 2018/0208716 A1    Jul. 26, 2018

Related U.S. Application Data

(60) Provisional application No. 62/450,539, filed on Jan. 25, 2017.

(51) Int. Cl.

| | | |
|---|---|---|
| *C08G 64/04* | (2006.01) | |
| *C08H 7/00* | (2011.01) | |
| *C07C 35/36* | (2006.01) | |
| *C08G 63/06* | (2006.01) | |
| *C08L 97/02* | (2006.01) | |
| *C08G 65/34* | (2006.01) | |
| *C07C 39/14* | (2006.01) | |

(52) U.S. Cl.
CPC .............. *C08G 64/04* (2013.01); *C07C 35/36* (2013.01); *C07C 39/14* (2013.01); *C08G 63/065* (2013.01); *C08G 65/34* (2013.01); *C08H 6/00* (2013.01); *C08L 97/02* (2013.01)

(58) Field of Classification Search
USPC ................................................. 528/196, 198
See application file for complete search history.

(56) References Cited

U.S. PATENT DOCUMENTS

| | | |
|---|---|---|
| 3,931,348 A | 1/1976 | Taniguchi et al. |
| 6,410,678 B1 | 6/2002 | Ishida et al. |
| 7,115,700 B2 | 10/2006 | Cella et al. |
| 9,249,080 B2 | 2/2016 | Mazanec et al. |
| 2016/0002162 A1 | 1/2016 | Tanzio et al. |
| 2016/0145496 A1 | 5/2016 | Sorensen |
| 2016/0184795 A1 | 6/2016 | Powell et al. |

FOREIGN PATENT DOCUMENTS

| | | |
|---|---|---|
| EP | 0 859 374 A2 | 8/1998 |
| JP | 05-201888 A | 8/1993 |
| JP | 2014-185325 A | 10/2014 |

OTHER PUBLICATIONS

Angelini et al., "Simplified synthesis of 1,1'[$^{14}$C]-methylene-di (2-naphthol). A radiochemical and kinetic approach", Journal of Labelled Compounds and Radiopharmaceuticals, 2004, vol. 47, No. 9, pp. 543-556.
Bridgewater, "Review of Fast Pyrolysis of Biomass and Product Upgrading", Biomass and Bioenergy, Mar. 2012, vol. 38, pp. 68-94.
Cahiez et al., "Iron-Catalyzed Alkylations of Aromatic Grignard Reagents", Angewandte Chemie, Jun. 4, 2007, vol. 46, No. 23, pp. 4364-4366.
Dickerson et al., "Catalytic Fast Pyrolysis: A Review", Energies, 2013, vol. 6, pp. 514-538.
Fukora et al., A Novel Non-phosgene Polycarbonate Production Process using By-product CO2 as Starting Material, Green Chemistry, 2003, vol. 5, No. 5, pp. 497-507.
Goldberg, Book Review of Chemistry and Physics of Polycarbonates, Herman Schnell. Interscience, New York, 1964, Journal of Polymer Science: Part A-1, vol. 5, 1067, pp. 399-400.
Gross et al., "Synthesis of High Molecular Weight Polycarbonate by Solid-State Polymerization", Macromolecules, 2001, vol. 34, No. 12, pp. 3916-3920.
Isikgor et al., "Lignocellulosic Biomass: A Sustainable Platform for the Production of Bio-based Chemicals and Polymers", Polymer Chemistry, 2015, vol. 6, No. 25, pp. 4497-4559.
Iwabuchi et al., "Transformation of Lignin-Derived Aromatics into Nonaromatic Polymeric Substances with Fluorescent Activities (NAPSFA) by *Pseudomonas* sp. ITH-SA-1", ACS Sustainable Chemistry & Engineering, 2015, vol. 3, No. 11, pp. 2678-2685.
Kim et al., "Ruthenium-Catalyzed Aminomethylation and Methylation of Phenol Derivatives Utilizing Methanol as the C1 Source", Advanced Synthesis & Catalysis, Mar. 2017, vol. 359, No. 5, pp. 798-810.
Kuhire et al., "New poly (ether urethane) s based on lignin derived aromatic chemicals via ab monomer approach: Synthesis and characterization", European Polymer Journal, Oct. 2015, vol. 71, pp. 547-557.
Lillwitz et al., "Production of Dimethyl-2,6-naphthalenedicarboxylate: Precursor to Polyethylene Naphthalate", Applied Catalysis A: General, 2001, vol. 221, pp. 337-358.
Liu et al., "Catalytic Fast Pyrolysis of Lignocellulosic Biomass", Chemical Society Reviews, 2014, vol. 43, No. 22. pages 7594-7623.
Llevot et al., "From Lignin-derived Aromatic Compounds to Novel Biobased Polymers", Macromolecular Rapid Communications, 2016, vol. 37, No. 1, pp. 9-28.
Miller, "Sustainable Polymers: Opportunities for the Next Decade", ACS Macro Letters, 2013, vol. 2, No. 6, pp. 550-554.
Mukarakate et al., "Catalytic Fast Pyrolysis of Biomass: The Reactions of Water and Aromatic Intermediates Produces Phenols", Green Chemistry, 2015 vol. 17, pp. 4217-4227.

(Continued)

*Primary Examiner* — Terressa Boykin
(74) *Attorney, Agent, or Firm* — Michael A. McIntyre

(57) ABSTRACT

The present disclosure relates to a dimer that includes a first hydroxyl-functionalized naphthalene group and a second hydroxyl-functionalized naphthalene group, where the first hydroxyl-functionalized naphthalene group and the second hydroxyl-functionalized naphthalene group are connected by a bridging group. The present disclosure also relates to a polymer synthesized using the dimer, as well as methods for synthesizing both the dimer and the polymer.

20 Claims, 6 Drawing Sheets

(56) References Cited

OTHER PUBLICATIONS

Nimlos, "Catalytic Fast Pyrolysis for Producing Renewable Fuels and Chemicals from Biomass", Presentation—University of Nevada, Reno, Apr. 22, 2016, pp. 1-53.

Pei et al., "Adsorption Characteristics of 1,2,4-trichlorobenzene, 2,4,6-trichlorophenol, 2-naphthol and Naphthalene on Graphene and Graphene Oxide", Carbon, 2013, vol. 51, pp. 156-163.

Premachandran et al., "Enzymatic Synthesis of Fluorescent Naphthol-Based Polymers", Macromolecules, 1996, vol. 29, No. 20, pp. 6452-6460.

Pu, "1,1'-Binaphthyl Dimers, Oligomers, and Polymers: Molecular Recognition, Asymmetric Catalysis, and New Materials", Chemical Reviews, 1998, vol. 98, No. 7, pp. 2405-2494.

Schneiderman et al., "50th Anniversary Perspective: There Is a Great Future in Sustainable Polymers", Macromolecules, 2017, vol. 50, No. 10, pp. 3733-3749.

Stoylkova et al., "Methylation of 2-naphthol Over Molecular Sieves", Catalysis Letters, 2000, vol. 69, Nos. 1-2, pp. 109-112.

Woo et al., "Melt Polymerization of Bisphenol-A and Diphenyl Carbonate in a Semibatch Reactor", Journal of Applied Polymer Science, 2001, vol. 8, No. 8, pp. 1253-1266.

Xu et al., "Hydrobromic Acid-catalyzed Friedel—Crafts Type Reactions of Naphthols", RSC Advances, 2014, vol. 4, pp. 1559-1562.

Zhang et al., "Catalytic Fast Pyrolysis of Prairie Cordgrass Lignin and Quantification of Products by Pyrolysis—Gas Chromatography—Mass Spectrometry", Energy & Fuels, 2014, vol. 28, pp. 1066-1073.

Zhang, "Essential Scientific Mapping of the Value Chain of Thermochemically Converted Second-generation Bio-fuels", Green Chemistry, 2016, vol. 18, pp. 5086-5117.

NAPHTHALENE-CONTAINING POLYMERS AND METHODS OF MAKING THE SAME

CROSS-REFERENCE TO RELATED APPLICATIONS

This application claims the benefit of U.S. Provisional Patent Application No. 62/450,539 filed Jan. 25, 2017, the contents of which are incorporated herein by reference in their entirety.

CONTRACTUAL ORIGIN

The United States Government has rights in this disclosure under Contract No. DE-AC36-08GO28308 between the United States Department of Energy and the Alliance for Sustainable Energy, LLC, the Manager and Operator of the National Renewable Energy Laboratory.

BACKGROUND

Currently, production of commodity chemicals relies primarily on fossil resources. For a successful transition from petroleum energy to renewable energy, sustainable production of commodity chemicals, molecular precursors, and materials is necessary. Lignocellulosic biomass is a potential candidate for the substitution of petroleum-sourced products due to its natural abundance and eco-compatibility. Conversion of lignocellulosic biomass into biofuels co-produces similar chemical products as petroleum refining processes, and additionally purveys a slate of molecules that are not produced in substantial quantities from established fossil refining processes. Naphthols, a prime example, are produced during lignocellulosic biomass conversion to biofuels and are currently used as molecular indicators, dies, and biomarkers and have applications in medicine, agriculture, and material science. Thus, developing value added products from bio-derived compounds, such as naphthols, and methods for producing such compounds plays an important role in the economic success of future bio-refineries.

SUMMARY

An aspect of the present disclosure is a dimer that includes a first hydroxyl-functionalized naphthalene group and a second hydroxyl-functionalized naphthalene group, where the first hydroxyl-functionalized naphthalene group and the second hydroxyl-functionalized naphthalene group are connected by a bridging group. In some embodiments of the present disclosure, the bridging group may be an aliphatic group.

In some embodiments of the present disclosure, the dimer may have a structure selected from

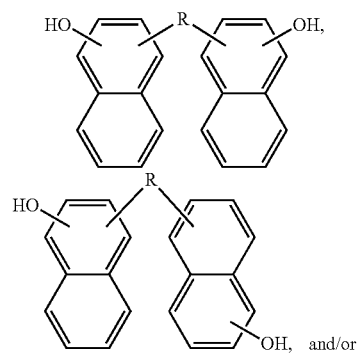

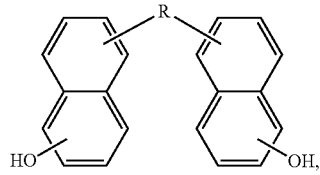

where R is the bridging group.

In some embodiments of the present disclosure, the structure of the dimer may be selected from

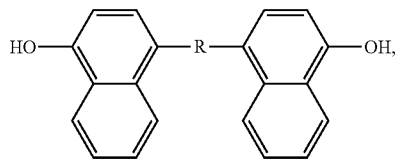

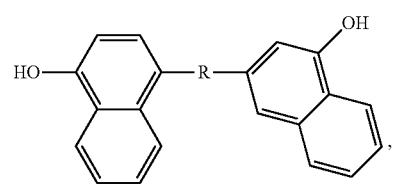

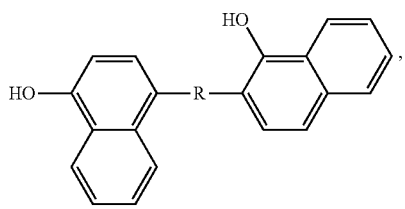

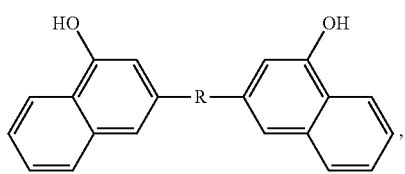

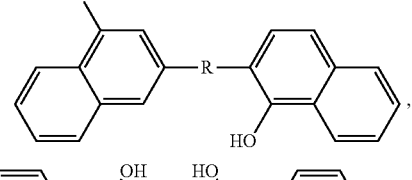

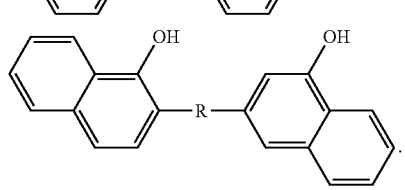

In some embodiments of the present disclosure, the structure of the dimer may be selected from

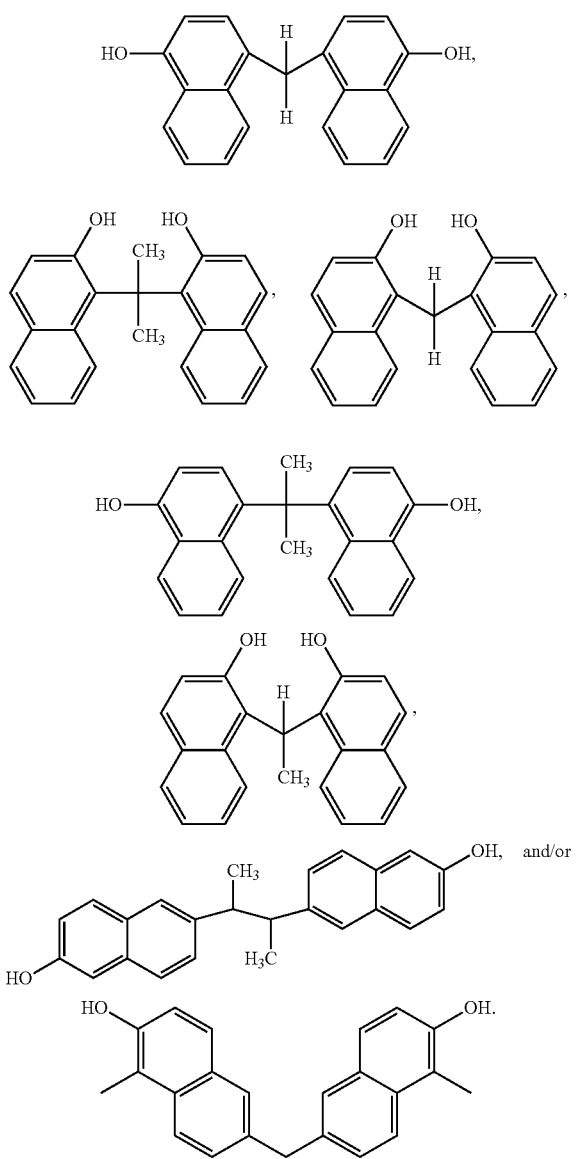

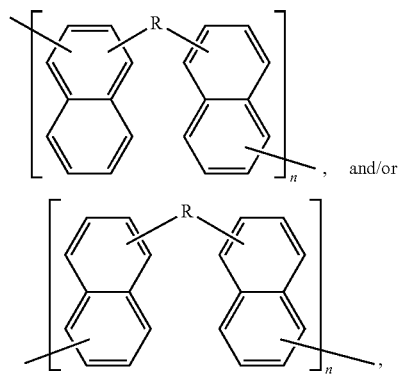, and/or where R is the bridging group and n is the number of units of the dimer.

In some embodiments of the present disclosure, the structure may be selected from

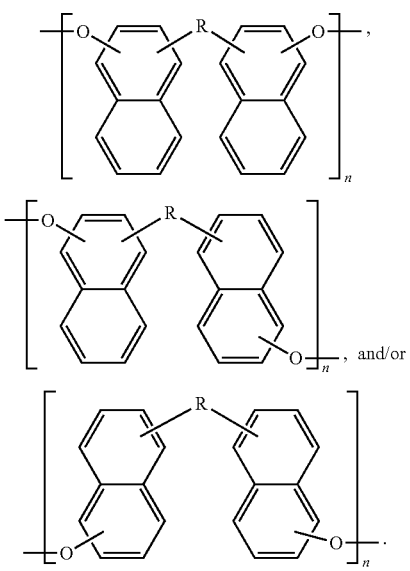

In some embodiments of the present disclosure, the structure may be selected from

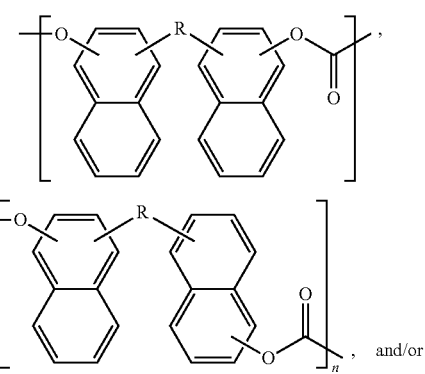

An aspect of the present disclosure is a polymer that includes a dimer that includes a first hydroxyl-functionalized naphthalene group and a second hydroxyl-functionalized naphthalene group, where the first hydroxyl-functionalized naphthalene group and the second hydroxyl-functionalized naphthalene group are connected by a bridging group, and where the polymer contains between 2 and 1500 units of the dimer, and the bridging group includes an aliphatic group.

In some embodiments of the present disclosure, the polymer has a structure that may be selected from

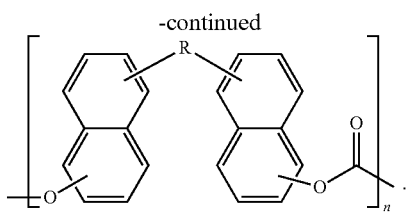

In some embodiments of the present disclosure, the polymer may be endcapped with at least one of a hydroxyl group, a halogen, an amine, and/or an oxygenated aromatic.

In some embodiments of the present disclosure, the polymer may have a structure selected from

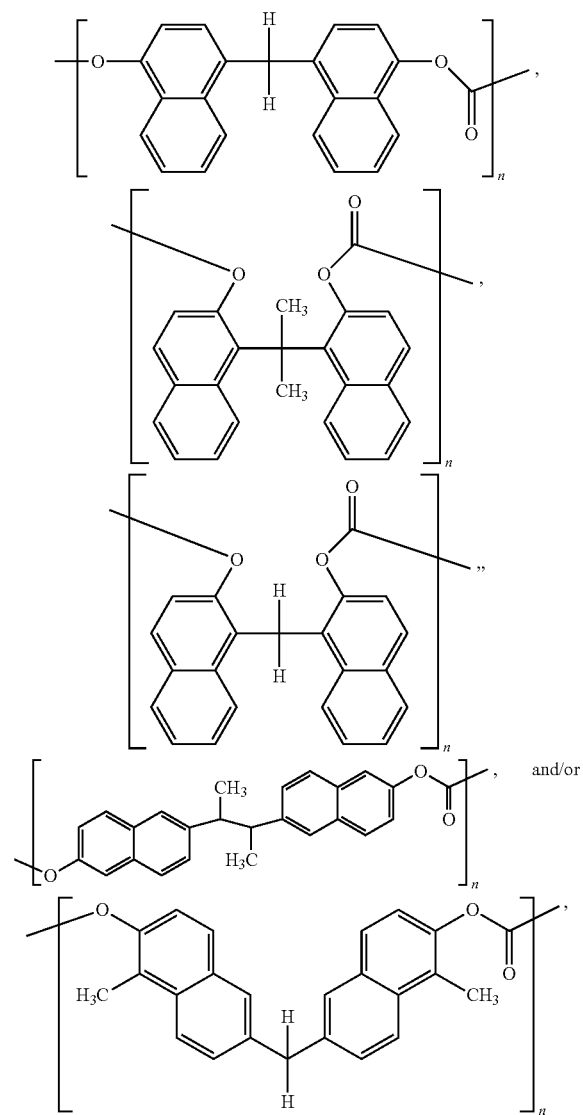

and/or wherein n is the number of units of the dimer.

In some embodiments of the present disclosure, the polymer may further include a weight averaged molecular weight, $M_W$, between 3 kDa and 400 kDa. In some embodiments of the present disclosure, the polymer may further include a degradation temperature between 150° C. and 500° C. In some embodiments of the present disclosure, the polymer may further include a glass transition temperature, $T_g$, between 50° C. and 200° C.

An aspect of the present disclosure is a method, where the method includes reacting a precursor molecule with a first bridging molecule to form a dimer, where the precursor molecule includes a hydroxyl-functionalized naphthalene, and the first bridging molecule includes at least one of a ketone, an aldehyde, and/or a halogenated aliphatic molecule. In some embodiments of the present disclosure, the precursor molecule may include at least one of a naphthol, methyl naphthalene, an ethyl naphthalene, a dimethyl naphthalene, a methyl naphthol, and/or a dimethyl naphthol.

In some embodiments of the present disclosure, the first bridging molecule may have the structure

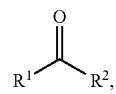

where $R^1$ includes a first aliphatic group, and $R^2$ includes a second aliphatic group.

In some embodiments of the present disclosure, the method may further include polymerizing the dimer with a second bridging molecule to produce a polymer, where the second bridging molecule may have the structure

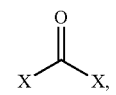

and X may include at least one of a hydroxyl group, a halogen, an amine, and/or an oxygenated aromatic. In some embodiments of the present disclosure, the second bridging molecule may include at least one of a carbonate and/or a phosgene.

An aspect of the present disclosure is a method for producing a dimer, where the method includes reacting 2-naphthol with Br2 to produce 6-bromonaphthalen-2-ol, reacting the 6-bromonaphthalen-2-ol to produce 2-bromo-6-methoxynaphthalene, reacting the 2-bromo-6-methoxynaphthalene with magnesium to produce 6-methoxynaphthalene, 2-MgBr, reacting the 6-methoxynaphthalene, 2-MgBr with 2,3-dibromobutane to produce 2,2'-(1,2-dimethyl-1,2-ethanediyl)di-(6-methoxynaphthalene), and reacting the 2,2'-(1,2-dimethyl-1,2-ethanediyl)di-(6-methoxynaphthalene) to produce the dimer comprising 6,6'-(butane-2,3,-diyl)di(naphthalen-2-ol).

BRIEF DESCRIPTION OF THE DRAWINGS

Exemplary embodiments are illustrated in referenced figures of the drawings. It is intended that the embodiments and figures disclosed herein are to be considered illustrative rather than limiting.

Figure 1:
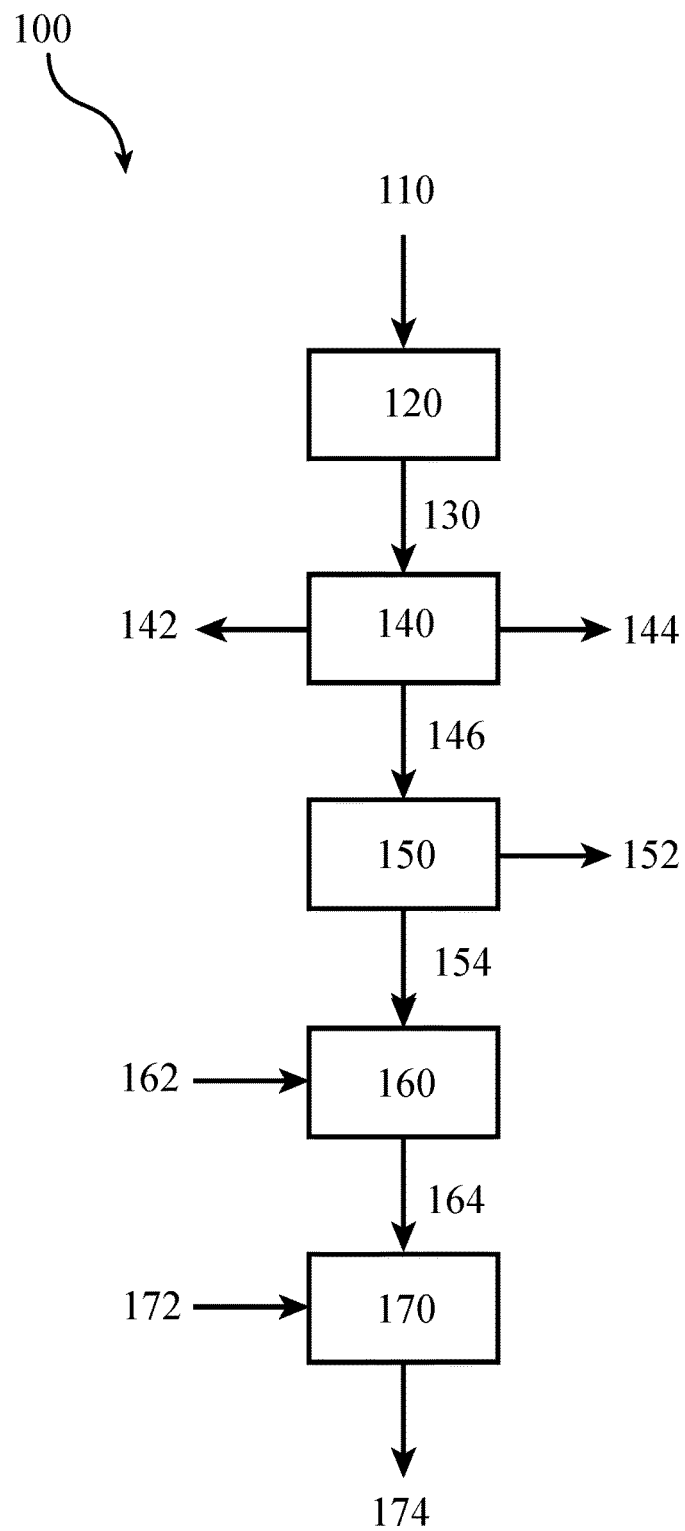
FIG. 1 illustrates a method for producing naphthalene-containing dimers and/or polymers from lignocellulosic biomass via CFP, according to some embodiments of the present disclosure.

REFERENCE NUMBERS 100 method
110 lignin-containing biomass
120 thermally treating
130 mixture
140 first separating
142 light organics
144 aqueous components
146 heavy organics
150 second separating
152 effluent stream
154 precursor molecule
160 reacting
162 first bridging molecule
164 dimer
170 polymerizing
172 second bridging molecule
174 polymer

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

As used herein, the term "isomers" includes any and all constitutional (structural), geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the present disclosure.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be a straight-chain (e.g., unbranched), branched, or cyclic (including fused, bridging, and spiro-fused polycyclic) and may be completely saturated or may contain one or more units of unsaturation, but which is not aromatic. Unless otherwise specified, aliphatic groups may contain 1-30 carbon atoms. In some embodiments, aliphatic groups may contain 1-12 carbon atoms. In some embodiments, aliphatic groups may contain 1-8 carbon atoms. In some embodiments, aliphatic groups may contain 1-6 carbon atoms. In some embodiments, aliphatic groups may contain 1-5 carbon atoms, in some embodiments, aliphatic groups may contain 1-4 carbon atoms, in yet other embodiments aliphatic groups may contain 1-3 carbon atoms, and in yet other embodiments aliphatic groups may contain 1-2 carbon atoms. Suitable aliphatic groups include, but are not limited to, linear or branched, alkyl, alkenyl, and/or alkynyl groups, and hybrids thereof such as (cycloalkyl)alkyl, (cycloalkenyl)alkyl and/or (cycloalkyl)alkenyl.

The term "polycyclic aromatic", as used herein, denotes a hydrocarbon ring structure with 1-5 rings. In some embodiments of the present disclosure, at least one ring may contain a partially or fully unsaturated carbon bond. In some embodiments, the unsaturated bonds may be conjugated. In some embodiments, the ring structure may contain 1-3 unsaturated bonds within the ring structure. In some embodiments, the ring structure may contain 3-7 carbon atoms. In some embodiments, the ring structure may have pendant groups, such as hydroxyls, carboxyls, ketones, methoxy, and/or amines substituted on the ring structure.

The term "oxygenate functionality", as used herein, denotes any moiety containing oxygen which is attached to aliphatic hydrocarbons or polycyclic aromatics.

The term "polymer", as used herein, refers to a molecule of high relative molecular mass, the structure of which comprises the multiple repetition of units derived, actually or conceptually, from molecules of low relative molecular mass. In some embodiments, a polymer is comprised of only one monomer species or unit (e.g. a naphthalene-containing dimer), however, mixtures of more than one unit fall within the scope of the present disclosure. In some embodiments, a polymer of the present invention may be a copolymer, terpolymer, heteropolymer, block copolymer, and/or tapered heteropolymer.

The term "prepolymer", as used herein, refers to a molecule of moderate relative molecular mass, the structure of which comprises the multiple repetition of units derived, actually or conceptually, from molecules of low relative molecular mass. In some embodiments, a prepolymer may be comprised of only 1-3 or 2-4 repeat unit of a polymer monomer species.

The term "dimer" as used herein, refers to a molecule which is comprised of two subunits (e.g. precursor molecules) synthesized from the same or different monomers. A dimer may be connected by a bridging group and/or by a covalent bond.

The term "alkyl," as used herein, refers to saturated, straight- or branched-chain hydrocarbon radicals derived from an aliphatic moiety containing between one and six carbon atoms by removal of a single hydrogen atom. In some embodiments of the present disclosure, alkyl groups may contain 1-12 carbon atoms. In some embodiments, alkyl groups may contain 1-8 carbon atoms. In some embodiments, alkyl groups may contain 1-6 carbon atoms. In some embodiments, alkyl groups may contain 1-5 carbon atoms, in some embodiments, alkyl groups may contain 1-4 carbon atoms, in some embodiments alkyl groups may contain 1-3 carbon atoms, and in some embodiments alkyl groups may contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "pendent group" as used herein, refers to any relatively small group of atoms covalently attached to a monomer, dimer, prepolymer or polymer structure. The pendent group may be reactive, or may be inert. In some embodiments, a pendent group may include an aliphatic, halogen, aromatic, oxygen, nitrogen, sulfur and/or phosphate functionality. The pendent group may or may not affect the intrinsic properties of a precursor molecule, dimer, prepolymer and/or polymer.

The term "bridging group" as used herein, refers to any bond or group of atoms which connects two monomers to form a dimer. In some embodiments the bridging group may or may not contain pendent groups. In some embodiments of the present disclosure, a bridging group may include at least one of an aliphatic group and/or a polycyclic aromatic group, and may include at least one pendant group.

In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in some embodiments, their recovery, purification, and use for one or more of the purposes disclosed herein.

As used herein, $M_W$ refers to the weight averaged molecular weight of a material, $M_n$ refers to the number averaged molecular weight of a material, and $M_p$ refers to the peak molecular weight of a material. As used herein, the term "glass transition temperature", $T_g$, refers to the temperature at which a polymer goes from an amorphous rigid state to a more flexible glassy state. As used herein, the term "degradation temperature" refers to the temperature at which covalent bonds begin to break within a polymer.

The present disclosure relates to routes and methods for synthesizing novel, value-added compounds from lignocellulosic derived naphthols and/or other hydroxyl group functionalized polycyclic aromatic hydrocarbons, to improve the overall economic viability of bio-fuel production. As described herein, naphthols are viable precursors for producing novel, value added naphthalene-containing compounds, including dimers, polymers, and/or resins, that may improve the economics of future bio-refineries while also expanding synthetic chemistry routes for producing polycyclic compounds.

Biomass is a source of readily available and renewable carbon. Therefore, utilization of biomass for the synthesis of new and existing materials is a promising technology for future products and processes. Lignocellulosic biomass offers potential as a source for a vast array of monomers that may serve as precursors to intermediates (e.g. dimers), as well as polymers and/or resins for use as plastics. Most plants fall under the category of lignocellulosic biomass meaning that their cell walls are composed of cellulose, hemicellulose, and lignin. The lignin component of lignocellulosic biomass is highly aromatic in structure and these aromatic molecules may provide an excellent source for replacing petroleum-based aromatic molecules. Aromatic molecules can also be created from the other components of biomass. In order to utilize the aromatics, the lignocellulosic biomass needs to be broken down to smaller molecules that may be processed, upgraded, and/or converted to final target molecules, polymers, and/or resins. Prior to the thermal degradation of the biomass, it may be fractionated into its three major components, cellulose, hemicellulose, and lignin, after which various methods may be used for upgrading these components to biofuels, chemicals, and/or other useful intermediates and/or products. There are numerous methods for degrading lignocellulosic biomass. One of these methods is catalytic fast pyrolysis (CFP), where pyrolysis refers to the thermal degradation of biomass, in the absence of oxygen ($O_2$), resulting in a mixture of degradation products, including aromatics, olefins, alkanes, polycyclic aromatics, and/or various oxygenated compounds.

Pyrolysis is typically a "single step" biomass conversion process for thermally degrading biomass to a mixture of precursor molecules. In CFP, the precursor molecules resulting from the degradation of biomass are passed, while in the vapor phase, over a catalyst that converts and/or upgrades at least a portion of the precursor molecules into one or more higher value molecules. Thus, a variety of commodity chemicals and other molecules may be produced during catalytic upgrading. The selection of the catalyst used in CFP results in the production of specific product mixtures and concentrations. Naphthalene,

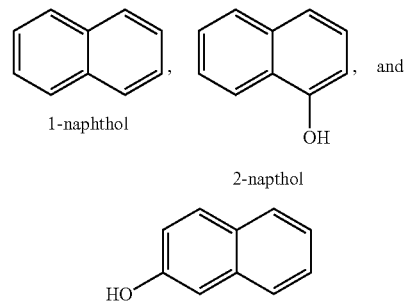

are examples of chemical monomers that may be produced by CFP and/or by the upgrading of CFP products. The polycyclic nature of naphthols and other oxygenated polycylic aromatic molecules (e.g. 1H-indenol, 2-hydroxyanthracene, 2-hydroxypyrene) make them suitable precursors for polymeric materials such as plastics. Phenol,

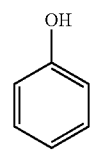

is a monomeric aromatic molecule (as opposed to polycyclic) that is produced in large quantities in petroleum refining. Naphthols are similar in structure to phenols. However, naphthols, like naphthalene, possess two benzene rings versus the one ring possessed by phenol. Phenol has many uses most relevant being its use as a precursor for producing bisphenol-A (BPA). BPA,

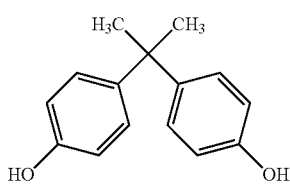 [SMILES: CC(C)(c1ccc(O)cc1)c1ccc(O)cc1]

is a precursor to a class of polymers called polycarbonates. Polycarbonates are an essential and very widely used type of polymer that fall into a class of polymers called thermoplastics. Polycarbonates are a rapidly growing class of thermoplastic engineering polymers due to their desirable physical properties such as high heat resistance, impact resistance, translucence, and stability. These physical properties make polycarbonates extremely useful as components of plastic bottles, data-storage devices, structural materials, and automobiles. Given their structural characteristics, as described herein, naphthols may be used to produce dimers, polymers, and/or resins having similar advantages and value as those offered by phenols. For example, the increased aromaticity of naphthols, and other hydroxyl group functionalized polycyclic aromatic hydrocarbons, may provide them with even higher hydrophobicity and heat resistant than phenol-derived polymers, which suggests that as dimers and/or as final polymers and/or resins, naphthols and other naphthalene-containing molecules may provide even better performance and physical property characteristics than phenol-sourced dimerized precursors, resins, and/or polymers.

FIG. 1 illustrates a method 100 for converting lignin-containing biomass 110 by thermally treating 120 the lignin-containing biomass 110 to a mixture 130. In some embodiments of the present disclosure, the thermally treating 120 may be accomplished by pyrolysis (e.g. catalytic fast pyrolysis) and/or gasification (e.g. substoichiometric amounts of the oxygen needed to completely combust the lignin-containing biomass 110). The mixture 130 may contain at least three generalized streams, which may be segregated into individual streams, heavy organics 146, light organics 142, and aqueous components 144, by a first separating 140 step. In some embodiments of the present disclosure, the heavy organics 146 separated from the mixture 130 resulting from the thermally treating may include at least one of naphthalene, naphthalene-containing compounds (e.g. 1-naphthol and/or 2-naphthol), and/or other oxygenated polycylic aromatic molecules.

Referring again to FIG. 1, the lignin-containing biomass 110 may include biomass such as agricultural waste, industrial waste, forest product residues, energy crops and/or residential waste. In general, the lignin-containing biomass 110 should contain a lignocellulosic and/or lignin fraction. The lignin-containing biomass 110 may be fed for thermally treating 120 to a reactor, such as a pyrolysis unit where the lignin-containing biomass 110 may be heated to high temperatures in the absence of oxygen ($O_2$) resulting in the degradation of lignin-containing biomass 110 to a mixture 130 of its various components such as various aromatics, alkanes, alkenes and/or oxygenated hydrocarbons. The mixture 130 resulting from the thermally treating 120 may contain at least some of the desired precursor molecules (e.g. at least one of 1-naphthol, 2-naphthol, and/or other hydroxyl group functionalized polycyclic aromatic hydrocarbons) for downstream conversion to at least one dimer (e.g. at least one dimer of two 1-naphthol molecules and/or 2-naphthols connected by a bridging molecule) and to at least one of naphthalene-containing polymers and/or naphthalene-containing resins. In some embodiments of the present disclosure, the mixture 130 resulting from the thermal treating 120 may be processed in a midstream upgrading process (not shown) to produce a target slate of precursor molecules where the yield of the target precursor molecules (e.g. at least one of 1-naphthol and/or 2-naphthol) are maximized. Regardless of whether midstream processing occurs or not, the mixture 130 containing the desired precursors molecules (e.g. at least one of 1-naphthol and/or 2-naphthol) may directed to a first separating 140 of the mixture 130 into at least two streams, a stream that includes light organics 142, a stream that includes aqueous components 144, and a stream that includes heavy organics 146. In some embodiment of the present disclosure, the heavy organics 146 may include the targeted precursor molecules (e.g. at least one of 1-naphthol and/or 2-naphthol). The first separating 140 may be performed by at least one unit operation, including distillation, liquid-liquid extraction, crystallization, and/or adsorption. A potential separation train may involve the fractionation of the mixture 130 via distillation. Removal of aqueous components may occur via liquid-liquid extraction resulting in a single and/or mixed component stream. In some embodiments of the present disclosure, the first separating 140 may involve recrystallization of a monomer from the mixture resulting in a highly pure precursor. The order and types of unit operations involved is subject to the desired precursor. Other unit operations and processes may be used to achieve the desired level of precursor purity. The first separating 140 may include a second separating 150, where the second separating 150 may use any of the separation methods and/or unit operations described above for the first separating 140, where the second separating 150 treats the heavy organics 146 to produce a relatively pure stream of the targeted precursor molecule 154 and effluent stream 152 containing substantially the remainder of the heavy organics 146. The effluent stream 152 may be directed to downstream operations for subsequent recovery and/or upgrading. Note, that although FIG. 1 illustrates the source of the targeted precursor molecule 154 being lignin-containing biomass 110, other sources for precursor molecules 154, e.g. petroleum based sources, also fall within the scope of the present disclosure.

In some embodiments of the present disclosure, the precursor molecules 154 may include at least one of an alkyl naphthalene, a naphthol, and/or an alkyl naphthol. In some embodiments of the present disclosure, the precursor molecules 154 may include at least one of methyl naphthalene, ethyl naphthalene, dimethyl naphthalene, methyl naphthol, and/or dimethyl naphthol. In some embodiments of the present disclosure, the precursor molecules 154 may include at least one of 1-methylnaphthalene, 2-methylnaphthalene, 2-ethylnaphthalene, 2,6-dimethylnaphthalene, 2,7-dimethylnaphthalene, and/or 1,8-dimethylnaphthalene. In some embodiments of the present disclosure, the precursor molecules 154 may include at least one of 1-naphthol or 2-naphthol. The precursor molecules 154 (e.g. a naphthalene-containing molecule) may then be directed to a process for reacting 160 at least a portion of the precursor molecules 154 with at least one first bridging molecule 162 to produce at least one dimer 164 (e.g. a naphthalene-containing dimer). As described herein, the dimer 164 may be produced by the union of one or more precursor molecules 154 (e.g. 1-naphthol and/or 2-naphthol). The reacting 160 of the precursor molecules 154 with a first bridging molecule 162 may be in the presence of a catalyst (not shown). In some embodiments of the present disclosure, the first bridging molecule 162 may include at least one of a ketone, an aldehyde, and/or a halogenated organic molecule. For example, a first bridging molecule 162 may include acetone, formaldehyde, acetaldehyde, glutaraldehyde, cyclopentanone, 2-cyclopenten-1-one and/or a dihalogenated organic molecule including 2,3-dibromobutane, 1,5-dichloropentane, and/or 1,2-dichloromethane. The reacting 160 may be catalyzed using an acid catalyst or a base catalyst. Examples of acid catalysts include acids in the liquid phase such as at least one of acetic acid, hydrochloric acid, sulfuric acid, nitric acid, hydrobromic acid, and/or perchloric acid. In some embodiments of the present disclosure a solid acid catalyst could be used including a sulfonated ion-exchange resin such as Amberlyst® and/or a fluorinated solid acid catalyst such as Nafion®. Base catalyst may include homogenous (e.g. sodium hydroxide, potassium hydroxide, ammonium hydroxide, calcium hydroxide) or heterogenous anion exchange resins (e.g. Amberlyst®, DOWEX®, Duolite®). The reacting 160 may be accomplished in any suitable reactor including at least one of a continuous packed bed reactor and/or a stirred tank reactor; e.g. either continuous or batch. The reacting 260 may be performed at a temperature between about 4° C. and about 200° C. or between about 40° C. and about 60° C. The reacting 160 may be performed at a pressure between about 0 bar (guage) and about 5 bar (guage) or at a pressure of about 1 atmosphere. The reaction may occur over 5 minutes to 24 hours. The reacting 160 may result in a naphthalene-containing dimer 164, for example at least one of a dimer of 1-naphthol and/or 2-naphthol. The specific dimer 164 produced will depend on the conditions of the reacting 160, the precursor molecules 154, and the first bridging molecules 162 used in the reacting 160. It is understood that many possible permutations and combinations of precursor molecules and first bridging molecules may exist and that these fall within the scope of the present disclosure.

For example, the dimer 164 resulting from the reacting 160 may include at least one of 4,4'-(propane-2,2-diyl)bis(naphthalen-1-ol), 1,1'-(propane-2,2-diyl)bis(naphthalen-2-ol), 1,1'-methylene-bis(naphthalen-1-ol), 1,1'-methylene-bis(naphthalen-2-ol), 1,1'-(ethane-1,1-diyl)bis(naphthalen-2-ol), 4,4'-(propane-2,2-diyl)bis(naphthalen-1-ol), and/or 1,1'-(propane-2,2-diyl)bis(naphthalen-2-ol). The dimer 164 may be a useful final product itself. However, in some embodiments of the present disclosure, at least one dimer 164 may be directed to a downstream process for polymerizing 170 the at least one dimer 164 (e.g. naphthalene-containing dimer) to a polymer 174. In some embodiments of the present disclosure, the polymer 174 may be cross-linked (e.g. a resin). Catalysts for the polymerizing 170 may include at least one of an alkali and/or alkaline earth compounds, anion exchange resins, alkoxy metals compounds, and/or tertiary amines. In some embodiments of the present disclosure, as described above, the polymerizing 170 may be completed by a condensation reaction. In some embodiments of the present disclosure, the polymerizing 170 may be completed by reacting the intermediate (e.g. naphthalene-containing dimer) with a second bridging molecule 172,

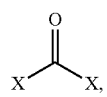

where x may include at least one of a halogen, an oxygenated aromatic, an amine, and/or an alcohol. In some embodiments, the second bridging molecules 172 may be alcohols such as primary, secondary, and/or tertiary alcohols, with examples of primary alcohols including methanol, ethanol, propanol, and/or butanol. In some embodiments, the second bridging molecule 172 may be a halogenated alcohol. Other examples of suitable second bridging molecules 172 include, but are not limited to phosgene, triphosgene, diphenyl carbonate, dimethyl carbonate, diethyl carbonate, or urea.

Thus, the present disclosure relates to methods for synthesizing dimers, polymers, prepolymers, and/or resins made by reacting and/or polymerizing the dimers. In some embodiments of the present disclosure, naphthalene-containing polymers and/or resins may be synthesized utilizing precursor molecules such as at least one of 1-naphthol, 2-napthol and/or other naphthalene-containing precursors and/or other hydroxyl group containing polycylic aromatic hydrocarbons. In some embodiments of the present disclosure, 1-napthol and 2-naphthol and various first bridging molecules are reacted to produce various hydroxyl-functionalized dimers with their hydroxyl groups available for downstream reacting and/or polymerizing, as described below.

In some embodiments of the present disclosure, 1-naphthol may react with a first bridging molecule to form a dimer according to the following reaction:

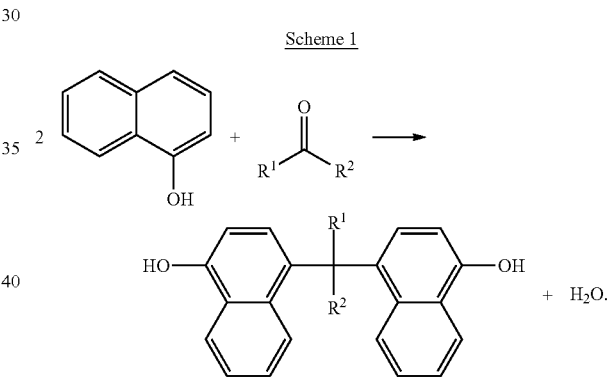

In some embodiments of the present disclosure, 2-naphthol may react with a first bridging molecule to form a dimer according to the following reaction:

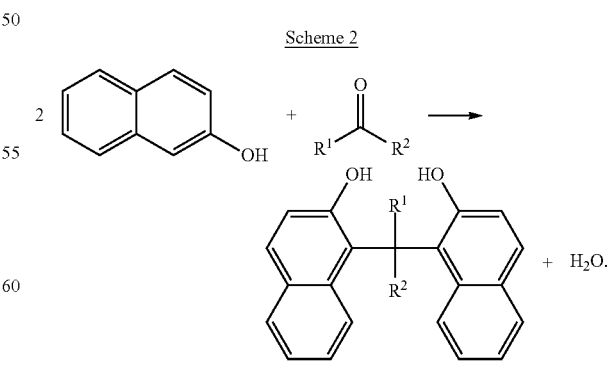

In Schemes 1 and 2, $R^1$ and $R^2$ may be independently selected, and may comprise an aliphatic group, for example an alkyl group such as a methyl group, and ethyl group, and/or a propyl. In some embodiments of the present disclosure, $R^1$ and $R^2$ may be at least one pendant group, for example, a pendant group having an oxygenate functionality.

Although Schemes 1 and 2 above show specific dimers resulting from the reaction of 1-naphthol and/or 2-naphthol, other variations of hydroxyl-containing dimers fall within the scope of the present disclosure. Examples of generalized structures of dimers, according to some embodiments of the present disclosure, include,

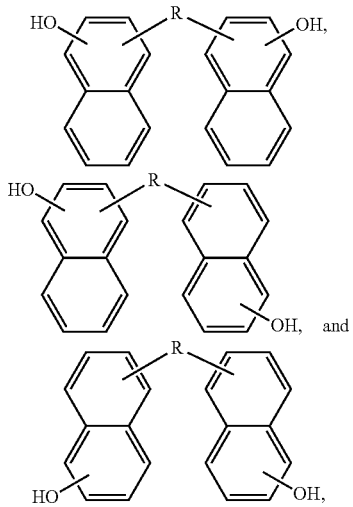

where R, a bridging group, in its simplest form may be a carbon atom, e.g. a —CH$_2$— group. However, other examples bridging groups include straight-chained, branched carbon chains and/or cyclic carbons, including saturated and/or unsaturated carbon chains (e.g. 1,2 dibromo butane, 1,4 dibromo propane, glutaraldehyde, cyclopentanone, 2-cyclopenten-1-one). The hydroxyl bonds and R-group bonds shown above, are shown terminating within the respective benzene rings to indicate Markush structures.

Examples of specific naphthalene-containing dimers, according to some embodiments of the present disclosure include,

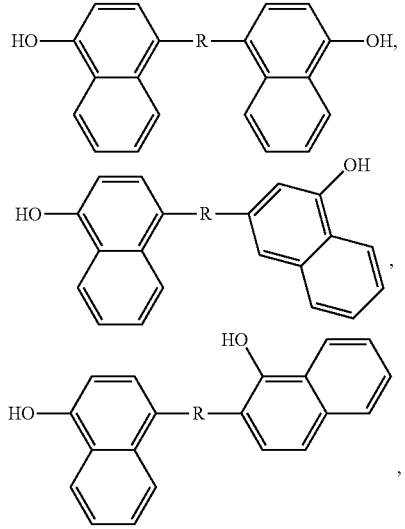

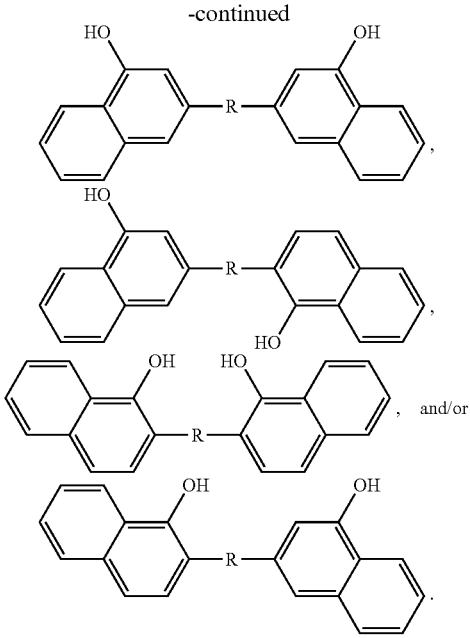

One or more dimers, as disclosed herein, may be subsequently polymerized to form a polymer. The polymerization of a dimer may be represented in general by the following three reactions, Scheme 3

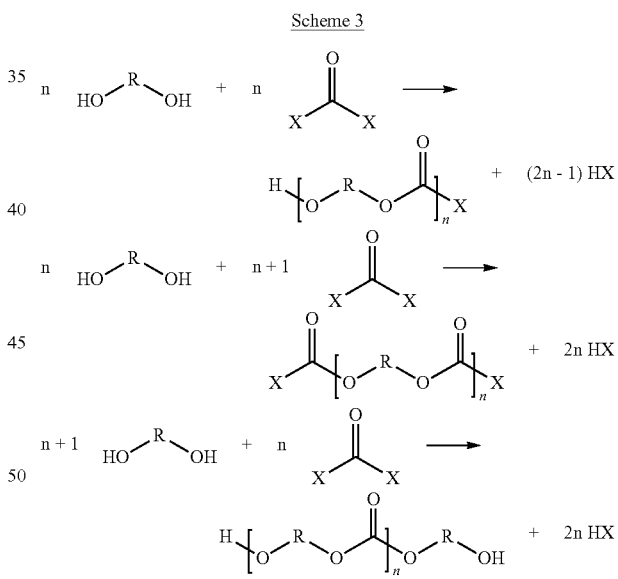

where, for these three generalized polymerization reactions, R represents the covalently linked naphthalene groups (a pair) for the dimer, as described above, and

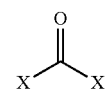

is a second bridging molecule. Thus referring to Scheme 3, in some embodiments of the present disclosure, a polymer may be endcapped with at least one of a hydroxyl group, a halogen, an amine, and/or an oxygenated aromatic.

Now illustrating the naphthalene containing dimer subunit, R, of Scheme 3, Schemes 4 and 5 illustrate two examples where one or more dimers may be polymerized by reaction with the second bridging molecule:

Scheme 4

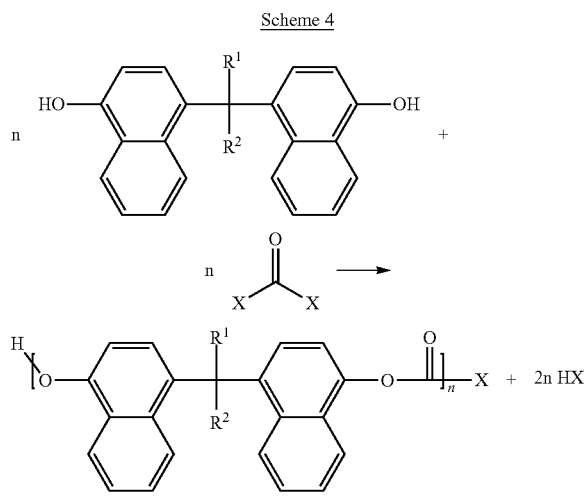

Scheme 5

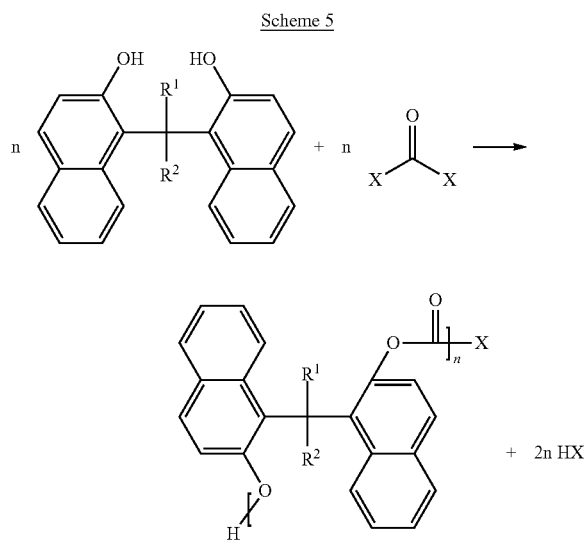

In some embodiments of the present disclosure, one or more dimers may be polymerized by a simple condensation reaction of the hydroxyl groups:

Scheme 6

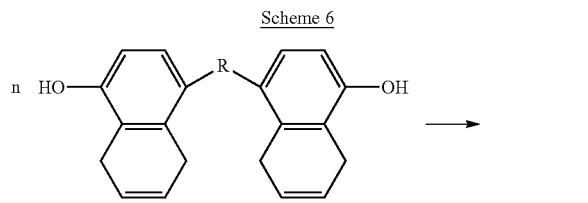

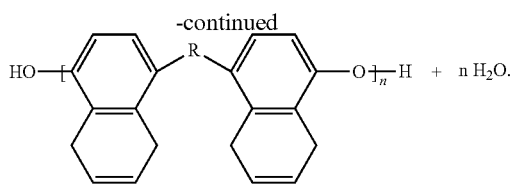

Referring again to Scheme 1, in some embodiments of the present disclosure, a precursor molecule, for example 1-naphthol, may be reacted with a first bridging molecule, for example a ketone having a first functional group $R^1$ and a second functional group $R^2$, to produce a naphthalene-containing dimer. In some embodiments of the present disclosure, $R^1$ and/or $R^2$ may be at least one of a hydrogen atom, a methyl group, an ethyl group, and/or a propyl group. $R^1$ and $R^2$ may be the same functional group or different. For the example where $R^1$ and $R^2$ are hydrogen, the naphthalene-containing dimer in Scheme 1 is 4,4'-methylene-bis(naphthalen-1-ol),

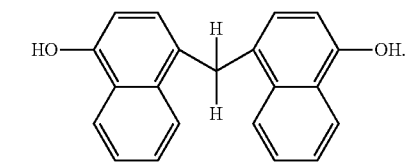 [SMILES: Oc1ccc(Cc2ccc(O)c3ccccc23)c2ccccc12]

For the example where $R^1$ and $R^2$ are methyl groups, the naphthalene-containing dimer in Scheme 1 is 1,1'-propylene-bis(naphthalen-2-ol),

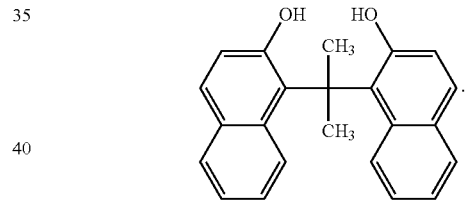

In some embodiments of the present disclosure, Scheme 1 may proceed to Scheme 4 by polymerizing the dimer with a second bridging molecule, such as a carbonate monomer (e.g. dimethyl carbonate, diphenol carbonate), phosgene, trichlorophosgene, as described above, to produce a polymer that includes repeat units of the dimer.

Scheme 2 above illustrates another example, the reaction of a precursor molecule, 2-naphthol, with a first bridging molecule, a ketone, to produce a naphthalene-containing dimer. For the example where $R^1$ and $R^2$ are hydrogen, the naphthalene-containing dimer in Scheme 2 is 1,1'-methylene-bis(naphthalen-2-ol) (abbreviated as 11'MB2N below),

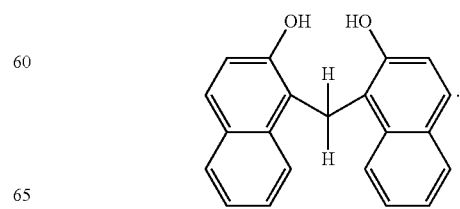

In some embodiments of the present disclosure, Scheme 2 may proceed to Scheme 5 by polymerizing the dimer with a second bridging molecule, as described above, to produce a polymer that includes repeat units of the dimer. The polymerization reactions for both Scheme 4 and 5 may proceed by adding the dimer, the second bridging molecule, and optionally a catalyst such as alkaline and alkaline earth metals (e.g. lithium hydroxide, calcium acetylacetonate, potassium hydrogenisophthalate), transition metals (e.g. lanthanum acetylacetonate), post-transition metals (e.g. tin(II) chloride, lead(II) acetylacetonate). The polymerization may proceed at pressures between full vacuum and atmospheric pressure with a temperature between 50° C. and 300° C.

Other examples of dimers that may be produced according to the methods described herein, include 4,4'-(propane-2,2-diyl)bis(naphthalen-1-ol)

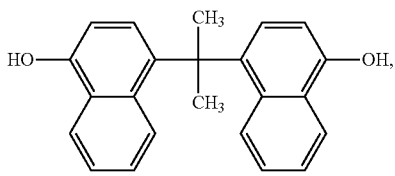 [SMILES: CC(C)(c1ccc(O)c2ccccc12)c1ccc(O)c2ccccc12]

1,1'-(ethane-1,1-diyl)bis(naphthalen-2-ol)

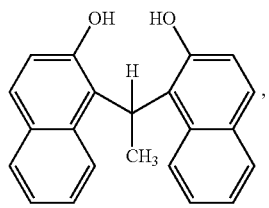 [SMILES: CC(c1c(O)ccc2ccccc12)c1c(O)ccc2ccccc12]

6,6'-(butane-2,3-diyl)bis(naphthalen-2-ol)

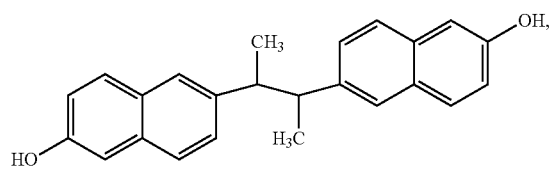 [SMILES: CC(c1ccc2cc(O)ccc2c1)C(C)c1ccc2cc(O)ccc2c1]

and 6,6'-methylenebis(1-methylnaphthalen-2-ol)

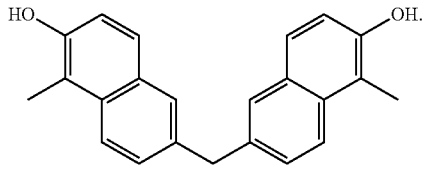 [SMILES: Cc1c(O)ccc2cc(Cc3ccc4c(C)c(O)ccc4c3)ccc12]

In some embodiments of the present disclosure, a naphthalene-containing polymer as described herein may have a glass transition temperature, $T_g$, between 50° C. and 200° C. In some embodiments of the present disclosure, a naphthalene-containing polymer as described herein may have a degradation temperature between 150° C. and 500° C. In some embodiments of the present disclosure, a naphthalene-containing polymer as described herein may include between 2 and 1500 repeat units (e.g. dimer). In some embodiments of the present disclosure, a naphthalene-containing polymer as described herein may have a weight averaged molecular weight, $M_W$, between 3 kDa and 400 kDa.

EXAMPLES

Materials: TMEDA, FeCl$_3$, 2-naphthol, 1-naphthol, 1,1'-methylene-bis(naphthalen-2-ol), 2-methoxy-6-bromonaphthalene, 1,2-dibromoethane, 2,3-dibromobutane, acetone, paraformaldehyde, acetic acid, acetaldehyde, HCl, THF, petroleum ether, and all other solvents were purchased from Sigma Aldrich and used without further purification.

Methods: All reactions (precursor to intermediate reactions) were carried out in a three-necked flask equipped with a condenser and a magnetic stir bar and under standard conditions unless stated otherwise. Obtained products were allowed to dry in a vacuum oven at 150° C. or 12 hours before any further characterization and were not purified to any extent beyond what is described in following synthetic methods.

Synthesis of 1,1'-methylene-bis(naphthalen-2-ol) Dimer

This dimer was produced according to the following reaction:

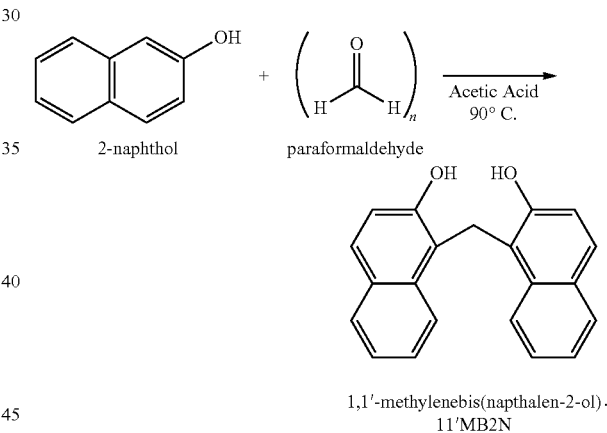

1,1'-methylenebis(napthalen-2-ol)· 11'MB2N

Figure 2:
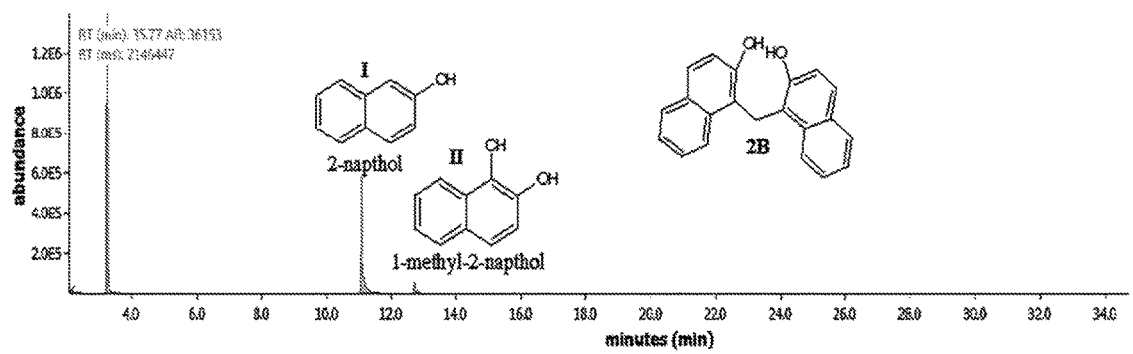
FIG. 2 illustrates a chromatogram from GC-MS characterization of dimers produced from napthols, according to some embodiments of the present disclosure.

Precursor molecule 2-naphthol (0.208 mmol) and acetic acid for a solvent and catalyst (20 mL) were charged to a 25 mL flask and the reaction temperature was set to 90° C. Once all 2-naphthol had dissolved and the reaction temperature had reached 90° C. paraformaldehyde (the first bridging molecule) (0.180 mmol) was added. After stirring for 1 hour the reaction mixture was allowed to cool to room temperature and a second aliquot of paraformaldehyde (0.030 mmol) was added. The reaction temperature was brought back to 90° C. then the reaction mixture was stirred for an additional 75 minutes. The reaction was then cooled to room temperature and acetic acid was evaporated under a gentle stream of nitrogen. The resultant products including 1,1'-methylene-bis(naphthalen-2-ol) were transferred to a sample vial. GC-MS results of the reaction products were compared to those observed for a standard of the target compound 1,1'-methylene-bis(naphthalen-2-ol). Peaks at two different retention times (RT) were observed in the standard chromatogram for 1,1'-methylene-bis(naphthalen-2-ol), shown in FIG. 2, as well as in the chromatogram from the reaction products. The two peaks represent the degradation products of 1-1'methylene-bis(napthaen-2-ol), those products being 2-naphthol and 1-methyl-2-naphthol. The degree of difference in observed $T_C$ and $T_M$ for the phenol standard and BPA standard is representative of the difference in $T_C$ and $T_M$ observed for 2-naphthol and the reaction products from R4. $T_M$ observed for the reaction products is 204.20° C. which is 50° C. higher than the $T_M$ observed for BPA, however as trans esterification and polymerization still occurs at temperatures above 204° C., 1,1'-methylene-bis(naphthalen-2-ol) has the potential to be utilized as a polycarbonate precursor. Several weight percent loss temperatures were observed for the reaction products during TGA characterization, all of which were above that observed for 2-naphthol. The latter indicates that the products obtained from this reaction either degrade or volatilize at a higher temperature than the starting material which is also an indication of successful dimerization and an increase in thermal stability from starting material to products.

1,1'-methylene-bis(naphthalen-2-ol) dimer was also produced under alkaline conditions according to the reaction,

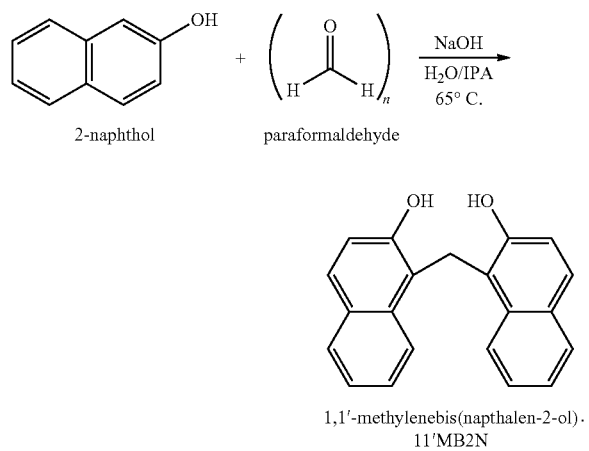

1,1'-methylenebis(napthalen-2-ol).
11'MB2N

The reaction proceeded rapidly, with product precipitating within twenty minutes. Analysis by NMR confirmed the identity of the product as 11'MB2N. The overall yield was found to be as high as 81%, with a purity above 99.5% as determined by differential scanning calorimetry (DSC).

Synthesis of
1,1'-(ethane-1,1-diyl)bis(naphthalen-2-ol) dimer 1,1'-(ethane-1,1-diyl)bis(naphthalen-2-ol) (11'EB2N) was produced according to the following reaction:

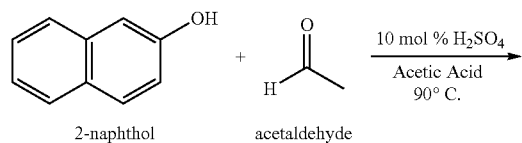

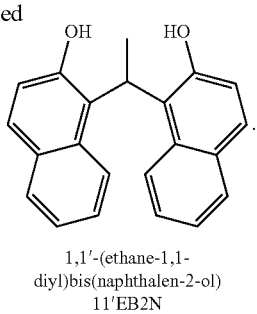

1,1'-(ethane-1,1-diyl)bis(naphthalen-2-ol)
11'EB2N

The bridging reaction of 2-naphthol and acetaldehyde under acidic conditions, however, did not proceed until after the addition of 10 mol % of catalytic $H_2SO_4$. After four hours, a small fraction of pure 1,1'-(ethane,1,1-diyl)bis(naphthalene-2-ol) was isolated and characterized by NMR.

Synthesis 6,6'-(butane-2,3-diyl)bis(naphthalen-2-ol) Dimer)

Figure 3:
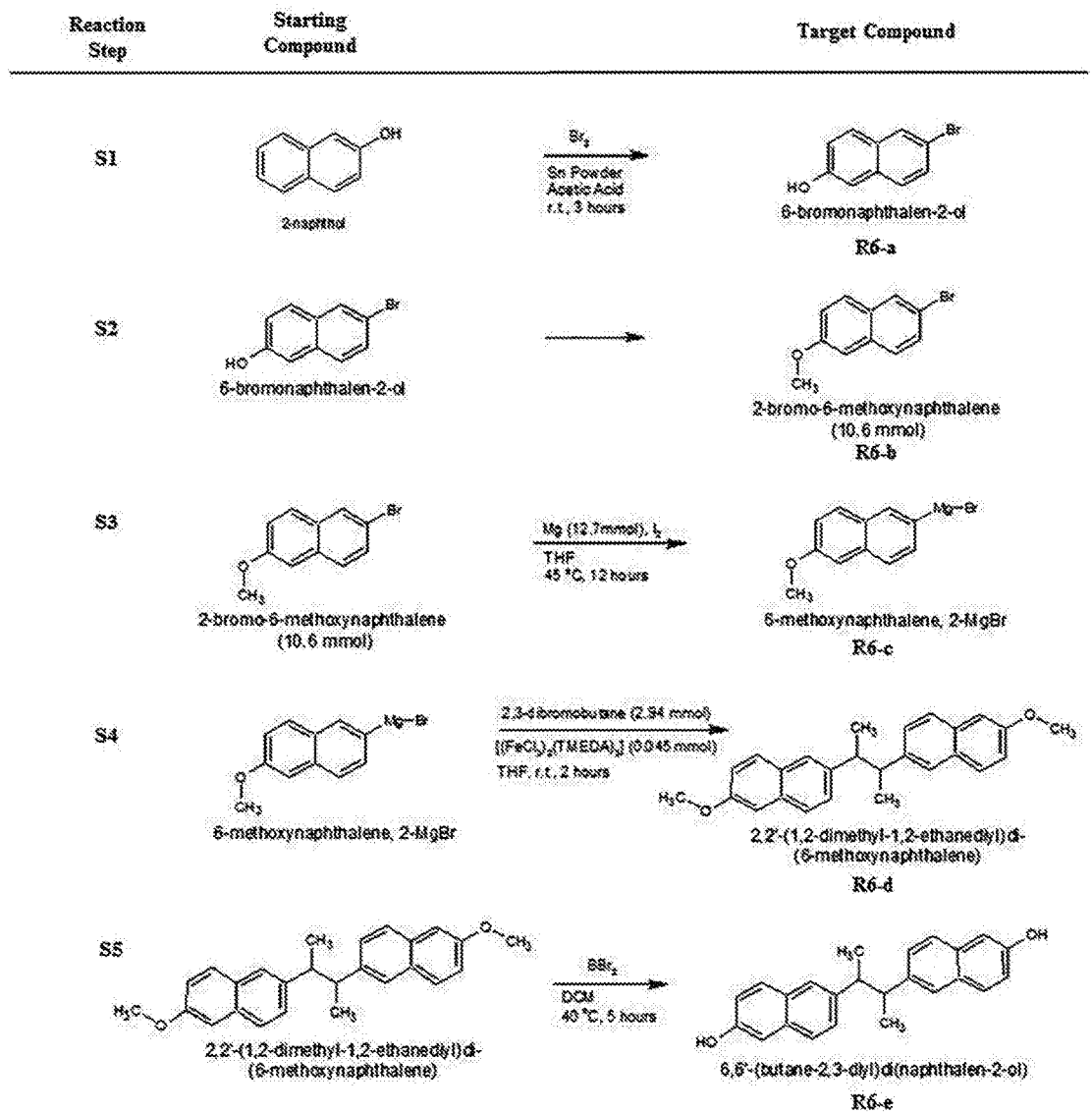
FIG. 3 illustrates synthetic routes for producing naphthalene-containing dimers, which may subsequently be converted to naphthalene-containing polymers, by reacting naphthols by Grignard chemistry, according to some embodiments of the present disclosure.

6,6'-(butane-2,3-diyl)bis(naphthalen-2-ol), illustrated above, may be synthesized in a multi-step process that begins with 2-naphthol as described below. This multi-step process is summarized in FIG. 3.

Preparation of R6-c from R6-b (See FIG. 3):

Magnesium (Mg) flakes (12.7 mmol) and a magnetic stir bar were charged to a 100 mL flask fitted with a dripping funnel and a jacketed condenser guarded with a calcium sulfate packed drying tube. A solution of 2-bromo-6-methoxynapthalene (10 mL, 1.06 M) in THF was then added to the dropping funnel and THF (2 mL) was added to the flask containing Mg and a stir bar. The Mg in THF was heated to 40° C. at which time about 1 mL of 2-bromo-6-methoxynapthalene solution (R6-b) was added to the reaction mixture drop wise. After 30 minutes an Grignard activating agent ($I_2$ or 1,2-dibromoethane) was added. After 3 hours the reaction mixture began to reflux vigorously and the reaction temperature was brought down to 35° C. The rest of solution of R6-b in the dripping funnel was then added to the reaction flask drop wise over 45 minutes. After a total of 12 hours and 45 minutes from the start of the reaction 4 mL of THF was added to the reaction and the reaction was stopped by removing the flask from the heat source. The resulting reaction mixture (solution R6-c), not including any unreacted Mg, was then transferred back into the dripping funnel.

Preparation of $[(FeCl_3)_2(TMEDA)_3]$.

Ferric chloride (10 mmol) and THF (100 mL) were charged to a 250 mL three-necked flask equipped with a magnetic stir bar and septums. The reaction mixture was stirred at room temperature. After the complete dissolution of ferric chloride TMEDA (15 mmol) was added dropwise over 3 minutes. The resulting solids were filtered and washed with THF and transferred to a sample vial.

Synthesis of R6-d from R6-c (see FIG. 3):

The reaction flask and drying tube from the setup used for the preparation of R6-C were both replaced with clean dry glassware. The clean reaction flask was charged with $[(FeCl_3)_2(TMEDA)_3]$ (0.0426 mmol), 2,3-dibromobutane (5.7 mmol), and THF (1 mL) then the reaction mixture was stirred on ice for 10 minutes. Once the $[(FeCl_3)_2(TMEDA)_3]$ appeared to have dissolved in the THF the dropping funnel was opened and solution R6-c was added dropwise over 90 minutes. The reaction mixture was allowed to stir for another 30 minutes following the addition of all of solution R6-c then the reaction was quenched with 25 mL of 1M HCl.

Figure 4:
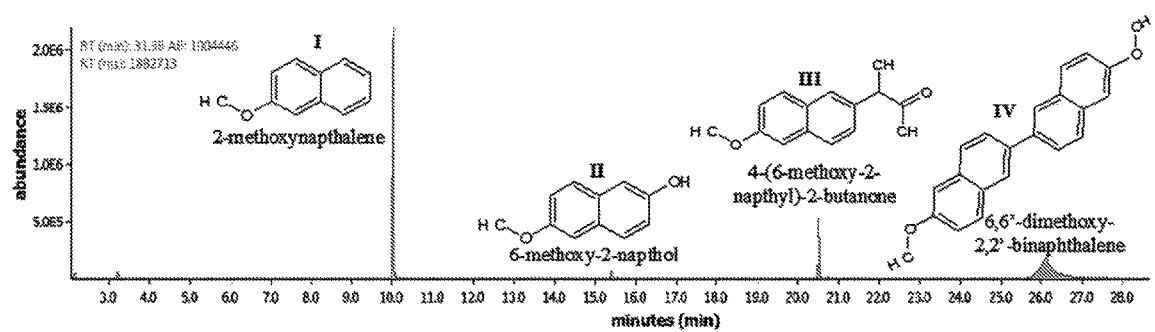
FIG. 4 illustrates a chromatogram from GC-MS characterization of dimers produced by reacting naphthols by Grignard chemistry, according to some embodiments of the present disclosure.

Separation of S4 Synthesis Products (See FIG. 3):

After the reaction was quenched all of the remaining solution was transferred to a separation funnel using 30 mL of petroleum ether (PE). The remaining solution was washed 4 times with 25 mL aliquots of PE and all organic washed were combined and transferred into a 250 mL round bottom flask. The petroleum ether was evaporated under vacuum leaving only and orange oil in the flask. The solution remaining in the separation funnel were washed 3 times with 25 mL aliquots of DI H$_2$O then mixed with 50 mL of THF. The remaining solids were then filtered out using vacuum filtration and washed with another 25 mL of THF. The remaining filtered solids were then transferred to a sample vial. Two reaction products were isolated; the oil extracted with petroleum ether (S4-oil) and the isolated white solids (S4-solids). S4-oil was characterized using GC-MS; the chromatogram is shown in FIG. 4. Several compounds were observed including the de-brominated starting material, shown in FIG. 10 as "I," the hydroxylated starting material, shown in FIG. 4 as "II," 4-(6-methoxy-2-naphthyl)-2-butanone, shown in FIG. 4 as "III," and the Wurtz side product of the formed Grignard reagent (R6-c) undergoing a homo-coupling reaction with its precursor R6-b, shown in FIG. 4 as "IV." FIG. 4 I, II, and III are likely products that resulted form quenching the reaction for the formation of R6-d with aqueous HCl. The observed peak for FIG. 4 as "III" indicated that a reaction between R6-c and 2,3-dibromobutane did occur. Since the latter is the first step in the synthesis of the dimer R6-d, it can be assumed that the formation of a methoxy-naphthyl-alkyl halide can occur under the conditions utilized and that the aforementioned first step is the slow step of the reaction. S4-solids were not able to be solubilized with any common organic solvents and therefore were not analyzed using GC-MS. S4-solids was also not de-methylated after separating it from the other reaction products, meaning that its properties will likely change once the hydroxyl groups are re-established as the terminal functional group (R6-E). It is difficult to conclude weather or not the weight loss observed via TGA characterization is indicative of volatilization or degradation. That being said, the TGA data indicated that S4-solids undergo rapid weight loss at about 26° C. greater than BPA which is promising for its potential as a polycarbonate precursor. DSC characterization of S4-solids also indicated promise of the unidentified solids as a potential polycarbonate precursor. Two $T_M$'s were observed indicating that the solids were not pure, or that there are two different crystalline compositions present. A single temperature observed for $T_C$ suggests that the latter is more likely. Both $T_M$'s measured for S4-solids were below typical trans-esterification and melt polymerization temperatures typical for polycarbonate formation. This indicated that the de-esterified derivative (R6-e) of S4-solids could be a potential candidate for a polycarbonate precursor.

Polymer Synthesis:

Utilizing the 1,1'-methylene-bis(naphthalen-2-ol) (11'MB2N) dimer synthesized previously, polymers were synthesized as described below. A melt polymerization technique was utilized which combined 11'MB2N and diphenyl carbonate (DPC) with 0.1 mol % of LiOH catalyst as shown:

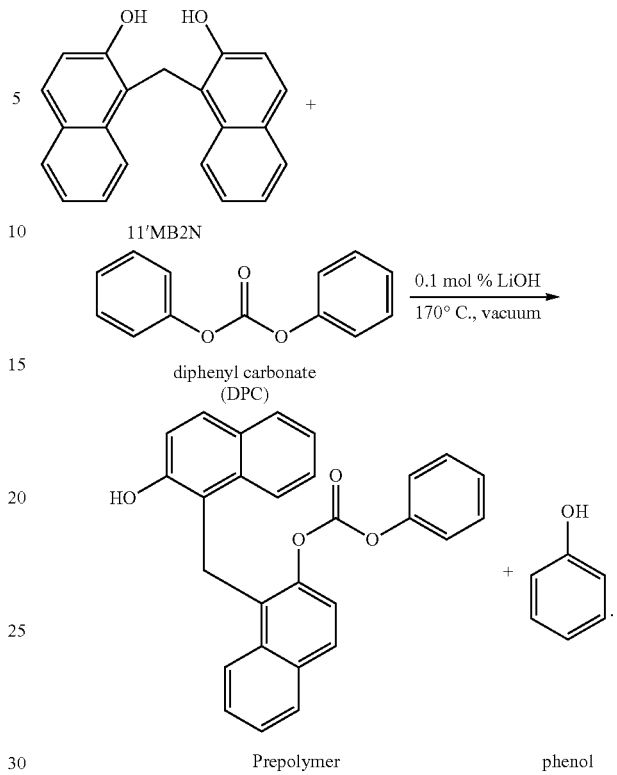

Figure 5A:
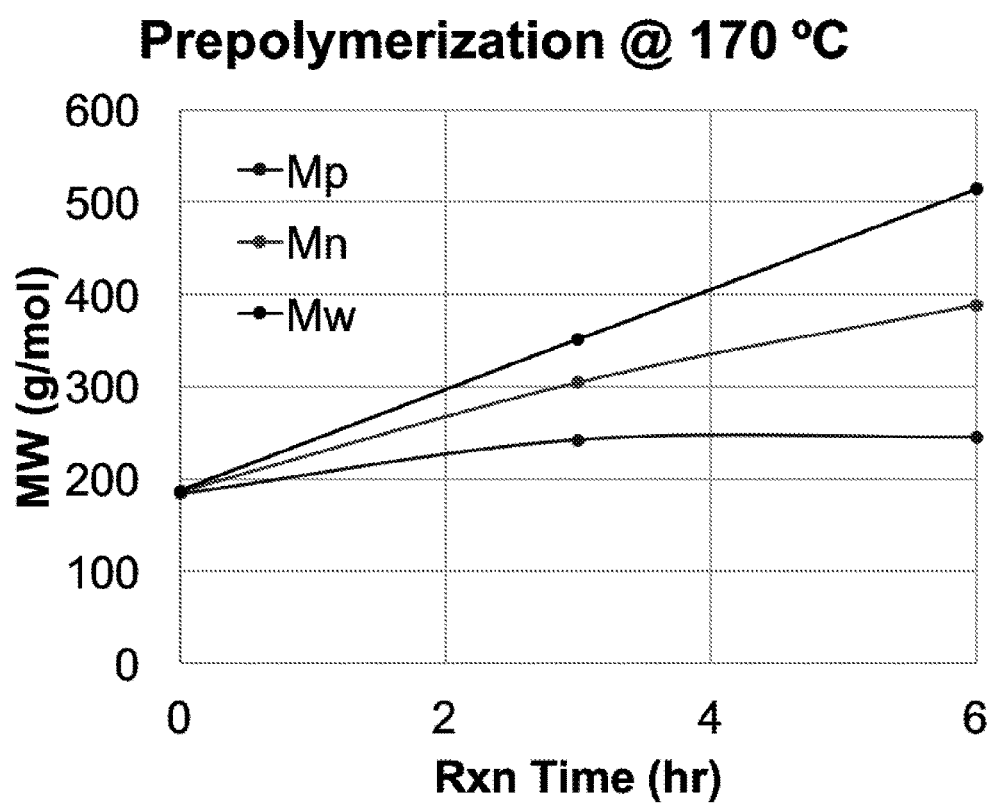
FIGS. 5A and 5B illustrate molecular weights for naphthalene-containing polymers produced from naphthalene-containing dimers, according to some embodiments of the present disclosure versus reaction time data for the prepolymerization (FIG. 5A) and polycarbonate (FIG. 5B) based on 1,1'-methylene-bis(naphthalen-2-ol) dimer. Peak molecular weight ($M_p$), number average molecular weight ($M_n$), and weight average molecular weight ($M_w$) were all determined from GPC analysis.

The initial melt polymerization was run under house vacuum at 170° C., or about 10-15° C. lower than the temperature at which 11'MB2N starts to degrade. This allowed for all reagents to melt into a viscous solution while avoiding degradation products. In this step, one of the hydroxyl groups on 11'MB2N is functionalized with a phenyl carbonate group to form a prepolymer structure that is recovered as an off-white solid. Analyzing the reaction over time using gel permeation chromatography (GPC) analysis, we saw that the weight ($M_w$) and number ($M_n$) average molecular weights of the largest reaction product increases over the six-hour reaction time (see FIG. 5A). The peak molecular weight ($M_p$) levels out after six hours, however. Higher temperatures and the removal of more phenol by vacuum may be necessary to push the molecular weight higher.

The next step, then, was to purify to prepolymer product and, now that it is functionalized with a carbonate group, to react the prepolymer at a higher temperature as shown below:

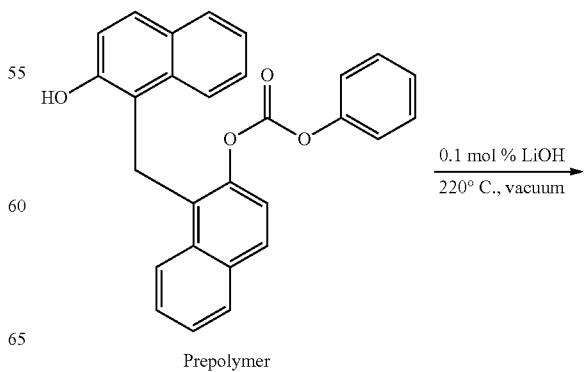

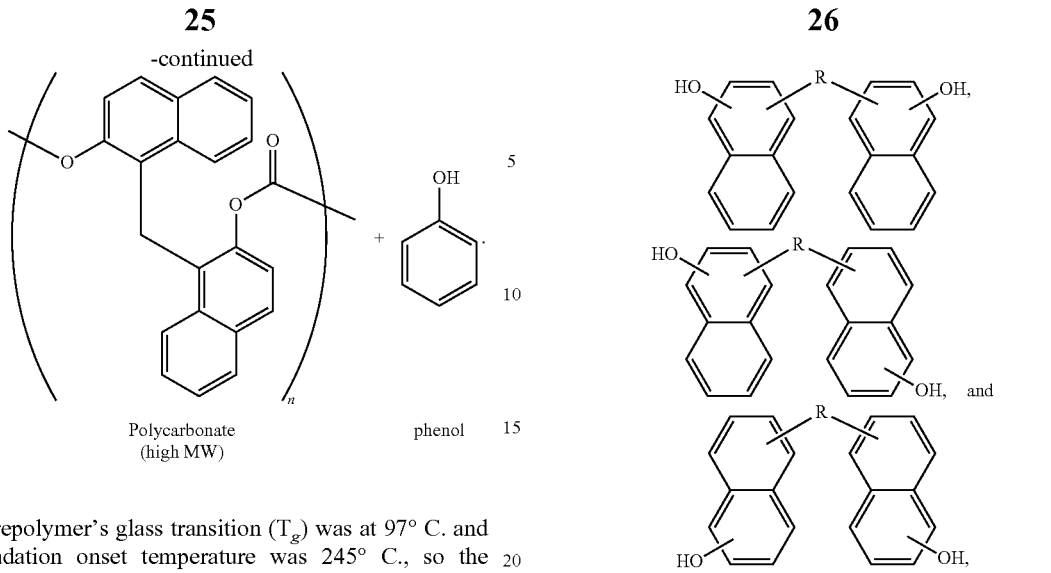

Polycarbonate (high MW)         phenol

Figure 5B:
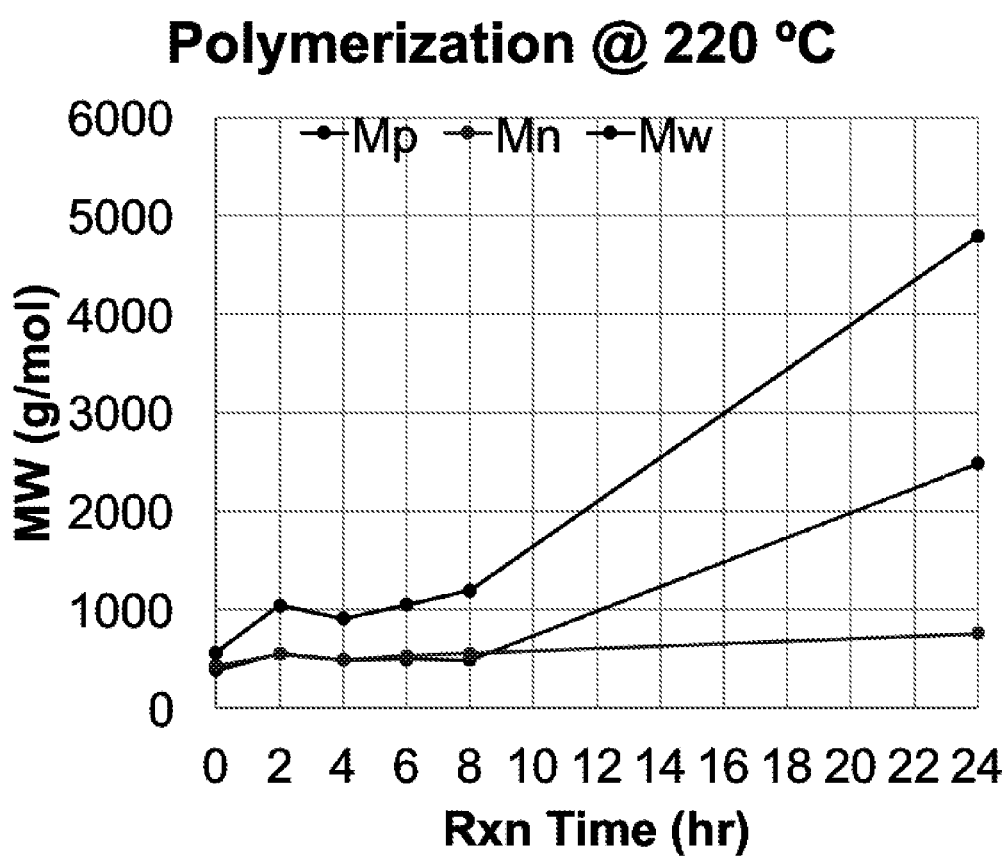

The prepolymer's glass transition ($T_g$) was at 97° C. and its degradation onset temperature was 245° C., so the polymerization reaction was completed at 220° C. A light brown to dark red polymer was recovered. The products of this reaction were recrystallized using dichloromethane and cold methanol and then analyzed by GPC showing a significant increase in $M_w$ and $M_p$, although $M_n$ increased at a much slower rate (FIG. 5B). The final $M_w$ of the synthesized polymer reached 4790 g/mol, which would correspond to a polymer containing eleven 11'MB2N subunits. The $T_g$ of the synthesized polymer was 209° C., which is high compared to BPA-polycarbonate's literature $T_g$ of 145° C. This suggests that the 11'MB2N polymer may have significant, and potentially beneficial, structural differences from BPA-polycarbonate.

Example 1

A dimer comprising: a first hydroxyl-functionalized naphthalene group; and a second hydroxyl-functionalized naphthalene group, wherein: the first hydroxyl-functionalized naphthalene group and the second hydroxyl-functionalized naphthalene group are connected by a bridging group.

Example 2

The dimer of Example 1, wherein the bridging group comprises an aliphatic group.

Example 3

The dimer of Example 2, wherein the aliphatic group comprises at least one of an alkyl group or an alkenyl group.

Example 4

The dimer of Example 3, wherein the alkyl group is selected from the group consisting of —$CH_2$—, —$C(CH_3)_2$—, —$C(CH_3)H$—, and —$C(CH_3)H$—$C(CH_3)H$—.

Example 5

The dimer of Example 1, wherein the dimer has a structure selected from the group consisting of and wherein R is the bridging group.

Example 6

The dimer of Example 5, wherein the structure is selected from the group consisting of

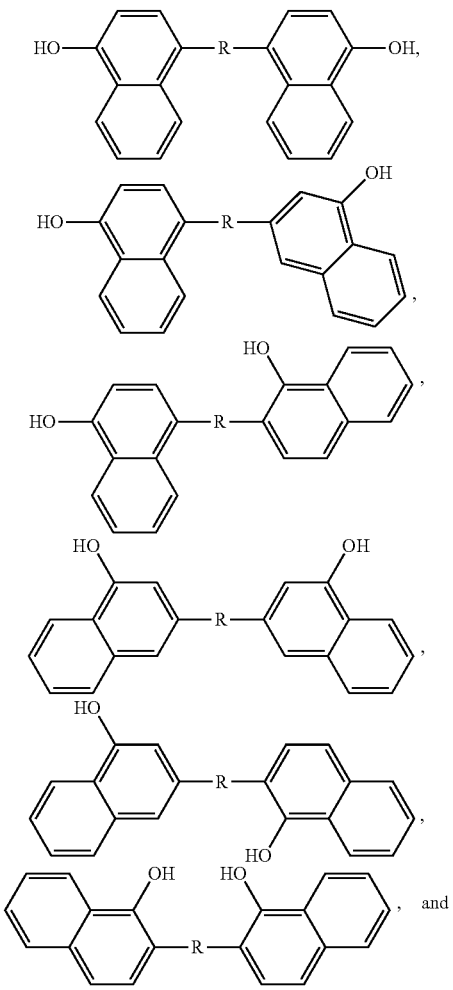

-continued

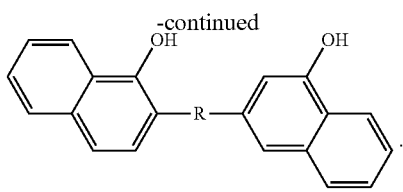

Example 7

The dimer of Example 5, wherein the structure is selected from the group consisting of

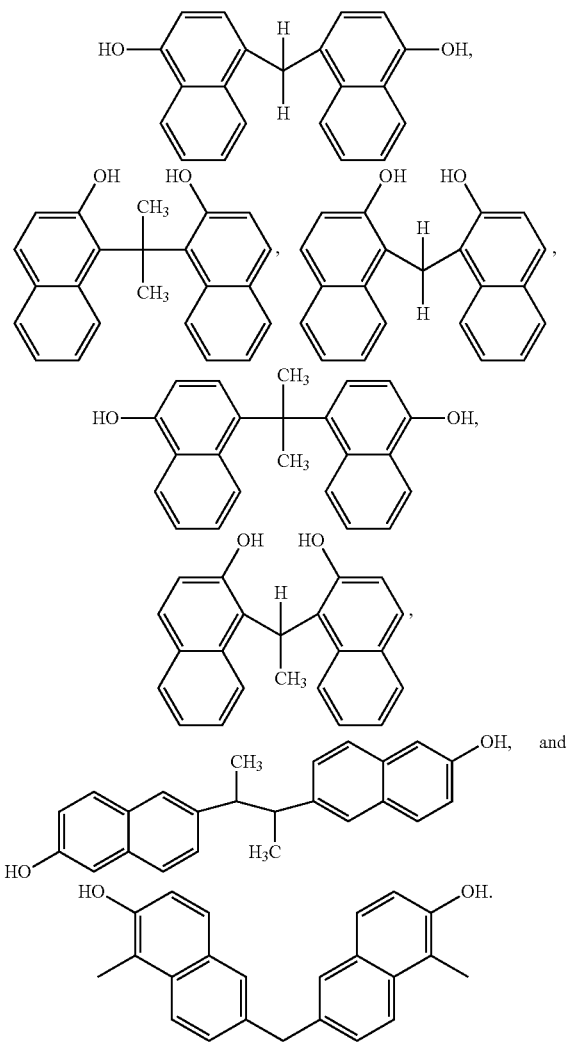

Example 8

The dimer of Example 1, wherein the dimer is selected from the group consisting of 4,4'-methylene-bis(naphthalen-1-ol), 1,1'-propylene-bis(naphthalen-2-ol), 1,1'-methylene-bis(naphthalen-2-ol), 4,4'-(propane-2,2-diyl)bis(naphthalen-1-ol), 1,1'-(ethane-1,1-diyl)bis(naphthalen-2-ol), 6,6'-(butane-2,3-diyl)bis(naphthalen-2-ol), and 6,6'-methylenebis(1-m ethylnaphthalen-2-ol).

Example 9

A polymer comprising: a dimer comprising: a first hydroxyl-functionalized naphthalene group; and a second hydroxyl-functionalized naphthalene group, wherein: the first hydroxyl-functionalized naphthalene group and the second hydroxyl-functionalized naphthalene group are connected by a bridging group, wherein: the polymer contains between 2 and 1500 units of the dimer, and the bridging group comprises an aliphatic group.

Example 10

The polymer of Example 9, wherein the units of the dimer are connected substantially in series.

Example 11

The polymer of Example 9, wherein the polymer has a structure selected from the group consisting of

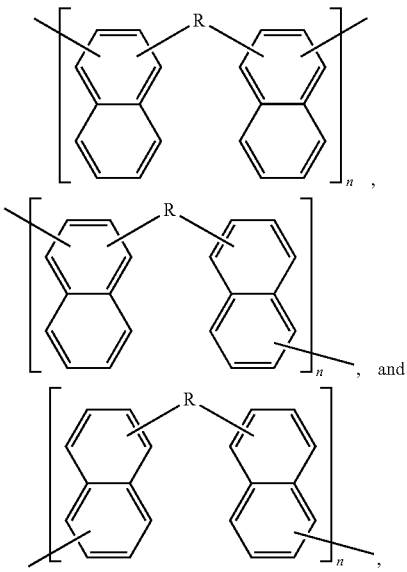

wherein R is the bridging group and n is the number of units of the dimer.

Example 12

The polymer of Example 11, wherein the structure is selected from the group consisting of

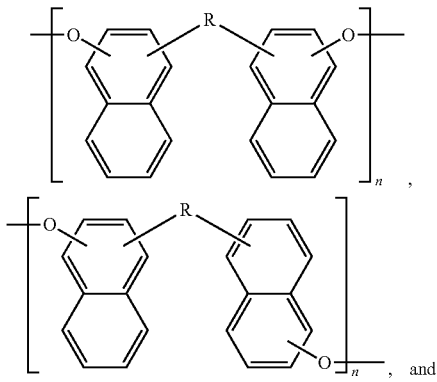

29

-continued

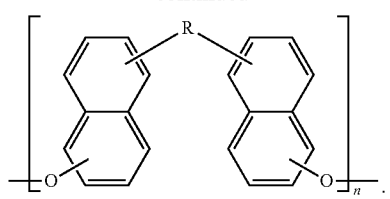

Example 13

The polymer of Example 12, wherein the structure is selected from the groups consisting of

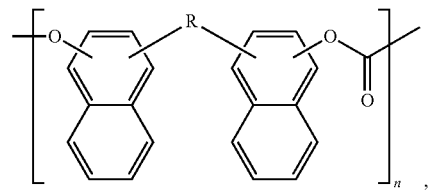

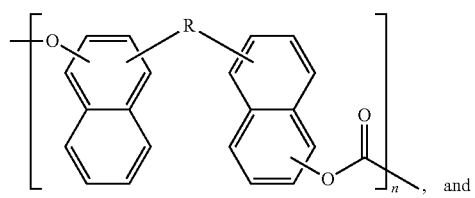

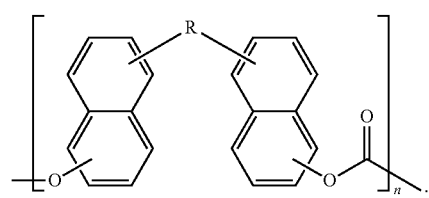

Example 14

The polymer of Example 11, wherein the polymer is endcapped with at least one of a hydroxyl group, a halogen, an amine, or an oxygenated aromatic.

Example 15

The polymer of Example 9, wherein the polymer has a structure selected from the group consisting of

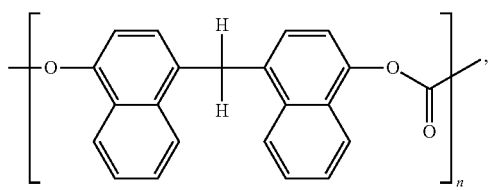

30

-continued

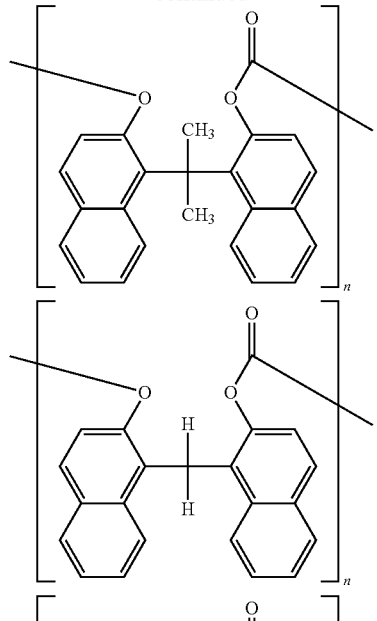

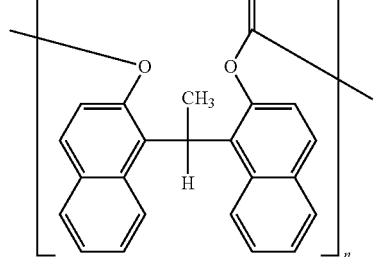

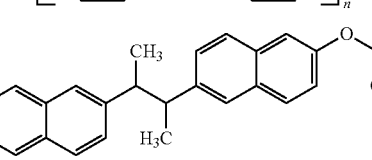

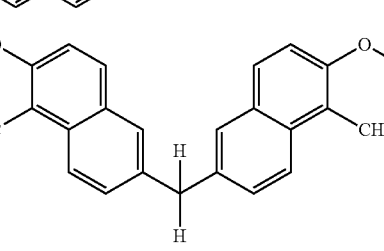

wherein n is the number of units of the dimer.

Example 16

The polymer of Example 9, further comprising a weight averaged molecular weight, $M_W$, between 3 kDa and 400 kDa.

Example 17

The polymer of Example 9, further comprising a degradation temperature between 150° C. and 500° C.

Example 18

The polymer of Example 9, further comprising a glass transition temperature, $T_g$, between 50° C. and 200° C.

Example 19

A method comprising: reacting a precursor molecule with a first bridging molecule to form a dimer, wherein: the precursor molecule comprises a hydroxyl-functionalized naphthalene, and the first bridging molecule comprises at least one of a ketone, an aldehyde, or a halogenated aliphatic molecule.

Example 20

The method of Example 19, wherein the precursor molecule comprises at least one of a naphthol, methyl naphthalene, an ethyl naphthalene, a dimethyl naphthalene, a methyl naphthol, or a dimethyl naphthol.

Example 21

The method of Example 20, wherein the precursor molecule comprises at least one of 1-naphthol or 2-naphthol.

Example 22

The method of Example 21, wherein the precursor molecule comprises at least one of 1-naphtol, 2-naphthol, 1-methylnaphthalene, 2-methylnaphthalene, 2-ethylnaphthalene, 2,6-dimethylnaphthalene, 2,7-dimethylnaphthalene, or 1,8-dimethylnaphthalene.

Example 23

The method of Example 19, wherein the first bridging molecule comprises at least one of acetone or formaldehyde.

Example 24

The method of Example 23, wherein the first bridging molecule comprises at least one of acetone, formaldehyde, acetaldehyde, glutaraldehyde, cyclopentanone, 2-cyclopenten-1-one, 2,3-dibromobutane, 1,5-dichloropentane, or 1,2-dichloromethane.

Example 25

The method of Example 19, wherein: the first bridging molecule has the structure

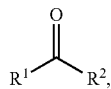

$R^1$ comprises a first aliphatic group, and $R^2$ comprises a second aliphatic group.

Example 26

The method of Example 19, wherein: the reacting further comprises a catalyst, and the catalyst comprises an acid catalyst or a base catalyst.

Example 27

The method of Example 26, wherein the acid catalyst comprises at least one of acetic acid, hydrochloric acid, sulfuric acid, nitric acid, hydrobromic acid, or perchloric acid.

Example 28

The method of Example 26, wherein the acid catalyst comprises at least one of a sulfonated ion-exchange resin or a fluorinated solid acid catalyst.

Example 29

The method of Example 26, wherein the base catalyst comprises a solution of at least one of sodium hydroxide, potassium hydroxide, ammonium hydroxide, or calcium hydroxide.

Example 30

The method of Example 26, wherein the base catalyst comprises an anion exchange resin.

Example 31

The method of Example 19, wherein the reacting is performed at a temperature between 4° C. and about 200° C.

Example 32

The method of Example 19, wherein the reacting is performed at a pressure between zero bar and 5 bar.

Example 33

The method of Example 19, wherein the dimer has a structure selected from the group consisting of

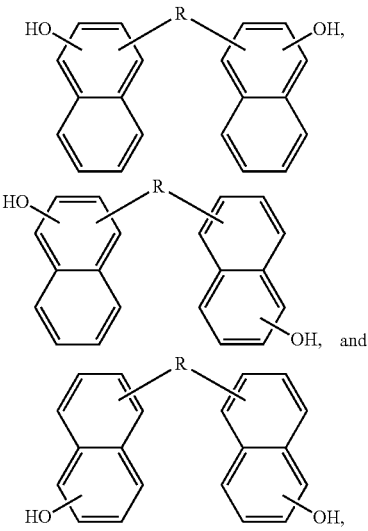

and wherein R is provided by the first bridging molecule.

Example 34

The method of Example 19, further comprising:
polymerizing the dimer with a second bridging molecule to produce a polymer, wherein: the second bridging molecule has the structure

and X comprises at least one of a hydroxyl group, a halogen, an amine, or an oxygenated aromatic.

Example 35

The method of Example 34, wherein the second bridging molecule comprises at least one of a carbonate or a phosgene.

Example 36

The method of Example 35, wherein the carbonate comprises at least one of dimethyl carbonate or diphenol carbonate.

Example 37

The method of Example 34, wherein: the polymerizing further comprises a catalyst, and the catalyst comprises at least one of alkaline, an alkaline earth metal, a transition metal, or a post-transition metal.

Example 38

The method of Example 37, wherein the catalyst for the polymerizing comprises at least one of lithium hydroxide, calcium acetylacetonate, potassium hydrogenisophthalate, lanthanum acetylacetonate, tin(II) chloride, or lead(II) acetylacetonate.

Example 39

The method of Example 34, wherein the polymerizing is performed at a temperature between 50° C. and 300° C.

Example 40

The method of Example 34, wherein the polymerizing is performed at a pressure between greater than full vacuum and atmospheric pressure.

Example 41

A method for producing a dimer, the method comprising: reacting 2-naphthol with Br$_2$ to produce 6-bromonaphthalen-2-ol; reacting the 6-bromonaphthalen-2-ol to produce 2-bromo-6-methoxynaphthalene; reacting the 2-bromo-6-methoxynaphthalene with magnesium to produce 6-methoxynaphthalene, 2-MgBr; reacting the 6-methoxynaphthalene, 2-MgBr with 2,3-dibromobutane to produce 2,2'-(1,2-dimethyl-1,2-ethanediyl)di-(6-methoxynaphthalene); and reacting the 2,2'-(1,2-dimethyl-1,2-ethanediyl)di-(6-methoxynaphthalene) to produce the dimer comprising 6,6'-(butane-2,3,-diyl)di(naphthalen-2-ol).

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicant in no way disclaims these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A dimer comprising:
   a first hydroxyl-functionalized naphthalene group; and
   a second hydroxyl-functionalized naphthalene group, wherein:
   the first hydroxyl-functionalized naphthalene group and the second hydroxyl-functionalized naphthalene group are connected by a bridging group.

2. The dimer of claim 1, wherein the bridging group comprises an aliphatic group.

3. The dimer of claim 1, wherein the dimer has a structure selected from the group consisting of

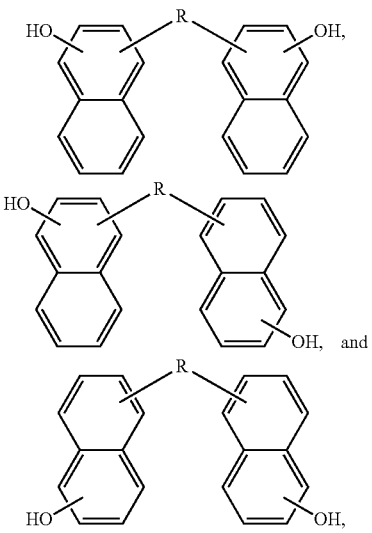

and wherein R is the bridging group.

4. The dimer of claim 3, wherein the structure is selected from the group consisting of

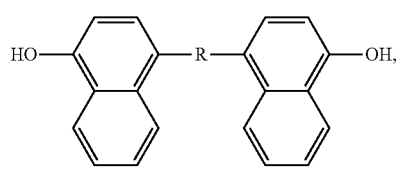

-continued

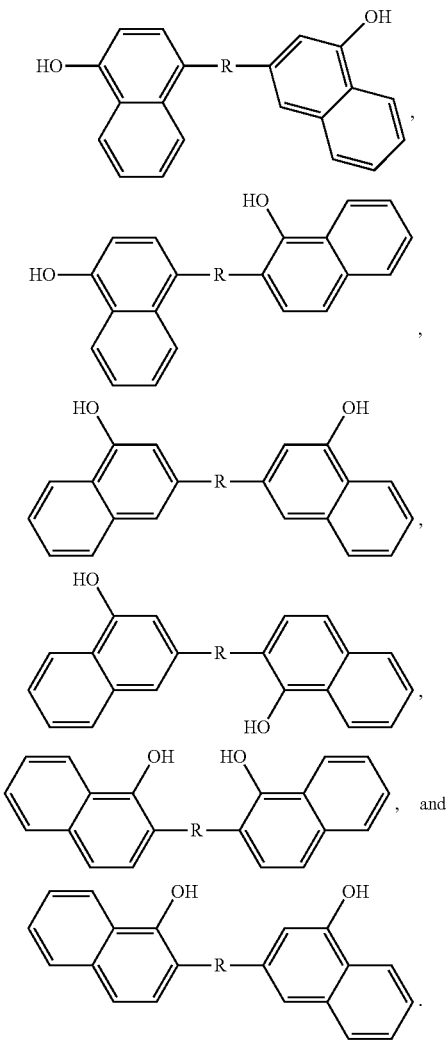

5. The dimer of claim 3, wherein the structure is selected from the group consisting of

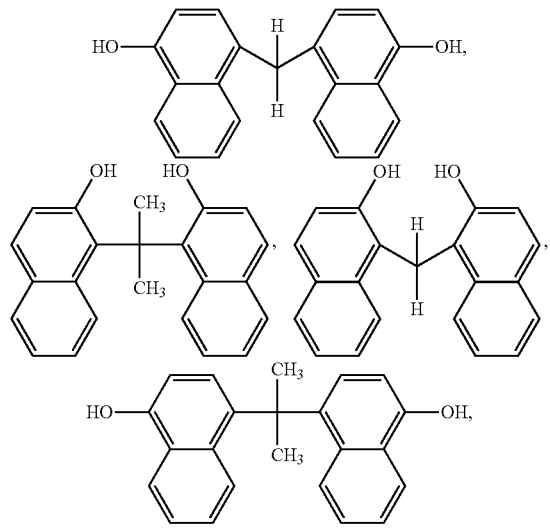

-continued

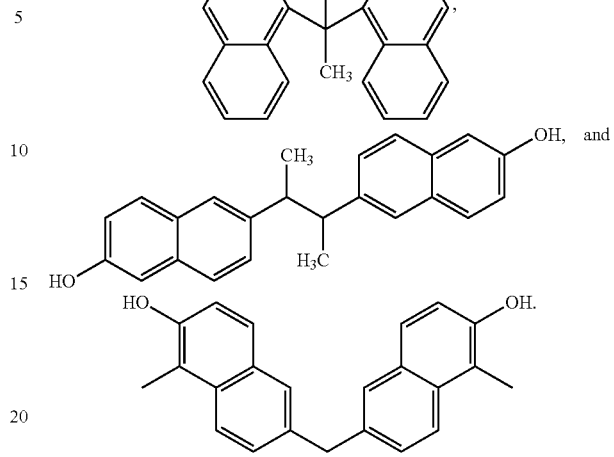

6. A polymer comprising:
a dimer comprising:
a first hydroxyl-functionalized naphthalene group; and
a second hydroxyl-functionalized naphthalene group, wherein:
the first hydroxyl-functionalized naphthalene group and the second hydroxyl-functionalized naphthalene group are connected by a bridging group, wherein:
the polymer contains between 2 and 1500 units of the dimer, and
the bridging group comprises an aliphatic group.

7. The polymer of claim 6, wherein the polymer has a structure selected from the group consisting of

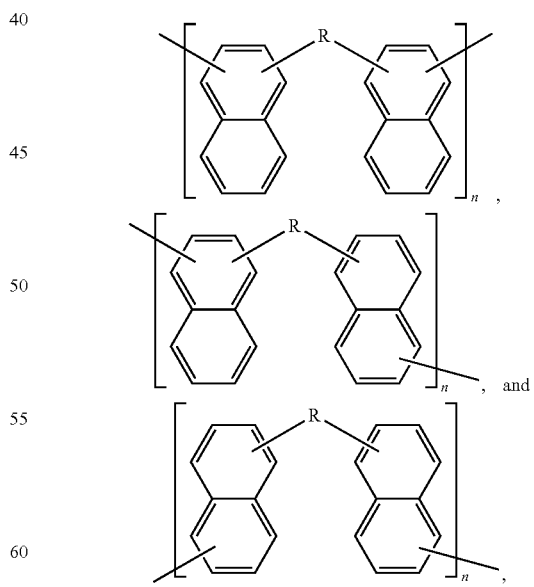

wherein R is the bridging group and n is the number of units of the dimer.

8. The polymer of claim 7, wherein the structure is selected from the group consisting of

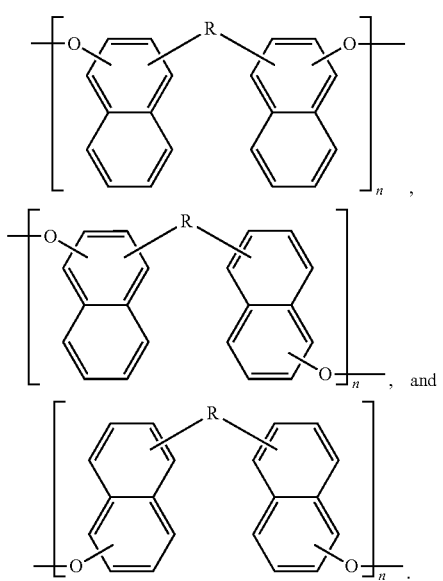

9. The polymer of claim 8, wherein the structure is selected from the groups consisting of

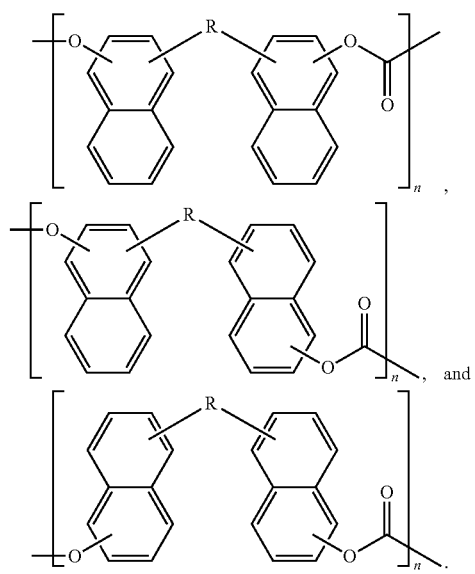

10. The polymer of claim 7, wherein the polymer is endcapped with at least one of a hydroxyl group, a halogen, an amine, or an oxygenated aromatic.

11. The polymer of claim 6, wherein the polymer has a structure selected from the group consisting of

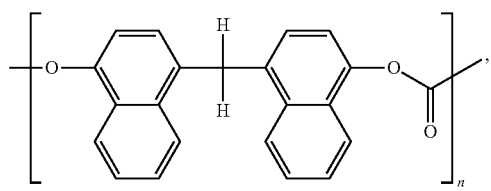

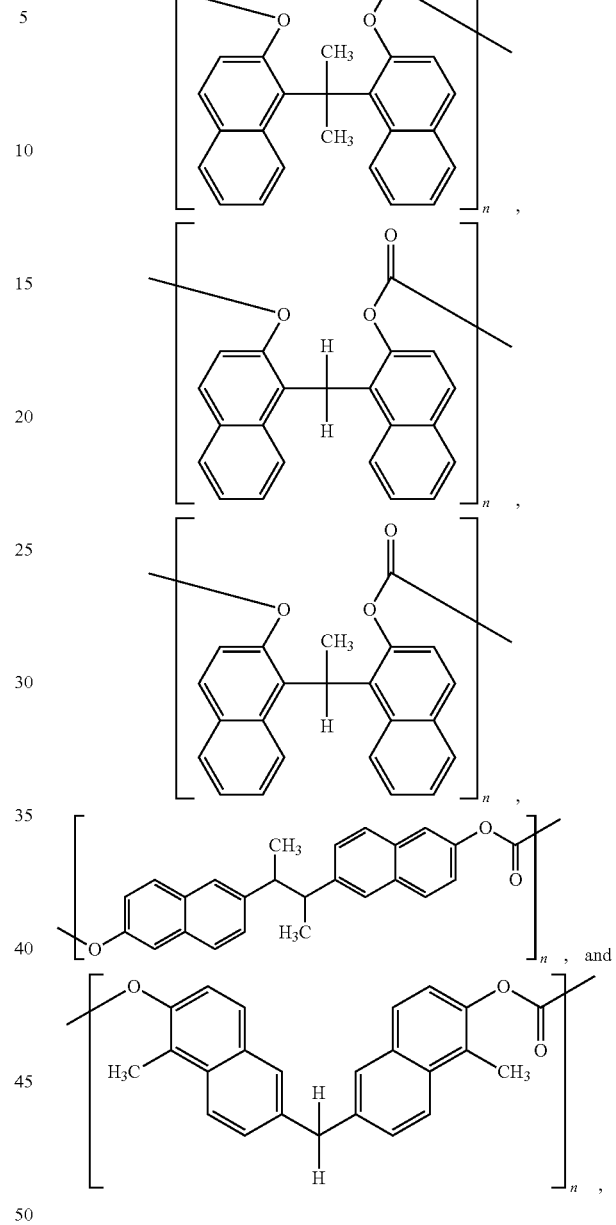

wherein n is the number of units of the dimer.

12. The polymer of claim 6, further comprising a weight averaged molecular weight, $M_W$, between 3 kDa and 400 kDa.

13. The polymer of claim 6, further comprising a degradation temperature between 150° C. and 500° C.

14. The polymer of claim 6, further comprising a glass transition temperature, $T_g$, between 50° C. and 200° C.

15. A method comprising:
reacting a precursor molecule with a first bridging molecule to form a dimer, wherein:
the precursor molecule comprises a hydroxyl-functionalized naphthalene, and
the first bridging molecule comprises at least one of a ketone, an aldehyde, or a halogenated aliphatic molecule.

16. The method of claim 15, wherein the second bridging molecule comprises at least one of a carbonate or a phosgene.

17. The method of claim 15, wherein:
the first bridging molecule has the structure

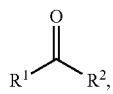

R¹ comprises a first aliphatic group, and
R² comprises a second aliphatic group.

18. The method of claim 15, further comprising:
polymerizing the dimer with a second bridging molecule to produce a polymer, wherein:
the second bridging molecule has the structure

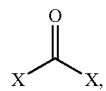

and
X comprises at least one of a hydroxyl group, a halogen, an amine, or an oxygenated aromatic.

19. The method of claim 16, wherein the precursor molecule comprises at least one of a naphthol, methyl naphthalene, an ethyl naphthalene, a dimethyl naphthalene, a methyl naphthol, or a dimethyl naphthol.

20. A method for producing a dimer, the method comprising:
reacting 2-naphthol with Br₂ to produce 6-bromonaphthalen-2-ol;
reacting the 6-bromonaphthalen-2-ol to produce 2-bromo-6-methoxynaphthalene;
reacting the 2-bromo-6-methoxynaphthalene with magnesium to produce 6-methoxynaphthalene, 2-MgBr;
reacting the 6-methoxynaphthalene, 2-MgBr with 2,3-dibromobutane to produce 2,2'-(1,2-dimethyl-1,2-ethanediyl)di-(6-methoxynaphthalene); and
reacting the 2,2'-(1,2-dimethyl-1,2-ethanediyl)di-(6-methoxynaphthalene) to produce the dimer comprising 6,6'-(butane-2,3,-diyl)di(naphthalen-2-ol).

* * * * *